United States Patent
Giataganas et al.

(10) Patent No.: US 12,380,998 B2
(45) Date of Patent: Aug. 5, 2025

(54) METHODS AND SYSTEMS FOR USING MULTIPLE DATA STRUCTURES TO PROCESS SURGICAL DATA

(71) Applicant: DIGITAL SURGERY LIMITED, London (GB)

(72) Inventors: Petros Giataganas, London (GB); Imanol Luengo Muntion, London (GB); Andre Chow, London (GB); Jean Nehme, London (GB); Danail Stoyanov, London (GB)

(73) Assignee: DIGITAL SURGERY LIMITED, London (GB)

( * ) Notice: Subject to any disclaimer, the term of this patent is extended or adjusted under 35 U.S.C. 154(b) by 729 days.

(21) Appl. No.: 17/491,658

(22) Filed: Oct. 1, 2021

(65) Prior Publication Data

US 2022/0020486 A1    Jan. 20, 2022

Related U.S. Application Data

(63) Continuation of application No. 16/292,108, filed on Mar. 4, 2019, now Pat. No. 11,189,379.
(Continued)

(51) Int. Cl.
*G16H 40/63* (2018.01)
*G06F 3/01* (2006.01)
(Continued)

(52) U.S. Cl.
CPC ............ *G16H 40/63* (2018.01); *G06F 3/014* (2013.01); *G06F 3/017* (2013.01); *G06F 16/22* (2019.01);
(Continued)

(58) Field of Classification Search
CPC ........ G16H 40/63; G16H 10/60; G16H 50/70; G16H 30/40; G06F 16/22; G06F 3/014;
(Continued)

(56) References Cited

U.S. PATENT DOCUMENTS

| 6,132,368 A | 10/2000 | Cooper |
| 6,206,903 B1 | 3/2001 | Ramans |

(Continued)

FOREIGN PATENT DOCUMENTS

EP    3537448 A1    9/2019

OTHER PUBLICATIONS

D. A. Nagy, I. J. Rudas and T. Haidegger, "OntoFlow, a software tool for surgical workflow recording," 2018 IEEE 16th World Symposium on Applied Machine Intelligence and Informatics (SAMI), Kosice and Herlany, Slovakia, 2018, pp. 000119-000124 (Year: 2018).*

(Continued)

*Primary Examiner* — Fonya M Long
*Assistant Examiner* — Anthony Balaj
(74) *Attorney, Agent, or Firm* — CANTOR COLBURN LLP

(57) ABSTRACT

The present disclosure relates to processing data streams from a surgical procedure using multiple interconnected data structures to generate and/or continuously update an electronic output. Each surgical data structure is used to determine a current node associated with a characteristic of a surgical procedure and present relevant metadata associated with the surgical procedure. Each surgical data structure includes at least one node interconnected to one or more nodes of another data structure. The interconnected nodes between one or more data structures includes relational metadata associated with the surgical procedure.

19 Claims, 7 Drawing Sheets

Related U.S. Application Data

(60) Provisional application No. 62/639,348, filed on Mar. 6, 2018.

(51) Int. Cl.

| | | |
|---|---|---|
| *G06F 16/22* | (2019.01) | |
| *G06N 5/02* | (2023.01) | |
| *G06V 20/40* | (2022.01) | |
| *G09B 9/00* | (2006.01) | |
| *G09B 23/28* | (2006.01) | |
| *G16H 10/60* | (2018.01) | |
| *G16H 30/40* | (2018.01) | |
| *G16H 50/70* | (2018.01) | |

(52) U.S. Cl.
CPC ............... *G06N 5/02* (2013.01); *G06V 20/41* (2022.01); *G06V 20/47* (2022.01); *G09B 9/00* (2013.01); *G09B 23/28* (2013.01); *G16H 10/60* (2018.01); *G16H 30/40* (2018.01); *G16H 50/70* (2018.01); *G06V 2201/10* (2022.01)

(58) Field of Classification Search
CPC ........ G06F 3/017; G06V 20/41; G06V 20/47; G06V 2201/10; G06N 5/02; G09B 9/00; G09B 23/28
See application file for complete search history.

(56) References Cited

U.S. PATENT DOCUMENTS

| | | | |
|---|---|---|---|
| 6,246,200 | B1 | 6/2001 | Blumenkranz et al. |
| 6,312,435 | B1 | 11/2001 | Wallace et al. |
| 6,331,181 | B1 | 12/2001 | Tierney et al. |
| 6,394,998 | B1 | 5/2002 | Wallace et al. |
| 6,424,885 | B1 | 7/2002 | Niemeyer et al. |
| 6,441,577 | B2 | 8/2002 | Blumenkranz et al. |
| 6,459,926 | B1 | 10/2002 | Nowlin et al. |
| 6,491,691 | B1 | 12/2002 | Morley et al. |
| 6,491,701 | B2 | 12/2002 | Tierney et al. |
| 6,493,608 | B1 | 12/2002 | Niemeyer |
| 6,565,554 | B1 | 5/2003 | Niemeyer |
| 6,645,196 | B1 | 11/2003 | Nixon et al. |
| 6,659,939 | B2 | 12/2003 | Moll et al. |
| 6,671,581 | B2 | 12/2003 | Niemeyer et al. |
| 6,676,684 | B1 | 1/2004 | Morley et al. |
| 6,685,698 | B2 | 2/2004 | Morley et al. |
| 6,699,235 | B2 | 3/2004 | Wallace et al. |
| 6,714,839 | B2 | 3/2004 | Salisbury, Jr. et al. |
| 6,716,233 | B1 | 4/2004 | Whitman |
| 6,728,599 | B2 | 4/2004 | Wang et al. |
| 6,746,443 | B1 | 6/2004 | Morley et al. |
| 6,766,204 | B2 | 7/2004 | Niemeyer et al. |
| 6,770,081 | B1 | 8/2004 | Cooper et al. |
| 6,772,053 | B2 | 8/2004 | Niemeyer |
| 6,783,524 | B2 | 8/2004 | Anderson et al. |
| 6,793,652 | B1 | 9/2004 | Whitman et al. |
| 6,793,653 | B2 | 9/2004 | Sanchez et al. |
| 6,799,065 | B1 | 9/2004 | Niemeyer |
| 6,837,883 | B2 | 1/2005 | Moll et al. |
| 6,839,612 | B2 | 1/2005 | Sanchez et al. |
| 6,840,938 | B1 | 1/2005 | Morley et al. |
| 6,843,403 | B2 | 1/2005 | Whitman |
| 6,846,309 | B2 | 1/2005 | Whitman et al. |
| 6,866,671 | B2 | 3/2005 | Tierney et al. |
| 6,871,117 | B2 | 3/2005 | Wang et al. |
| 6,879,880 | B2 | 4/2005 | Nowlin et al. |
| 6,899,705 | B2 | 5/2005 | Niemeyer |
| 6,902,560 | B1 | 6/2005 | Morley et al. |
| 6,936,042 | B2 | 8/2005 | Wallace et al. |
| 6,951,535 | B2 | 10/2005 | Ghodoussi et al. |
| 6,974,449 | B2 | 12/2005 | Niemeyer |
| 6,991,627 | B2 | 1/2006 | Madhani et al. |
| 6,994,708 | B2 | 2/2006 | Manzo |
| 7,048,745 | B2 | 5/2006 | Tierney et al. |
| 7,066,926 | B2 | 6/2006 | Wallace et al. |
| 7,084,884 | B1 | 8/2006 | Nelson et al. |
| 7,118,582 | B1 | 10/2006 | Wang et al. |
| 7,121,832 | B2 | 10/2006 | Hsieh et al. |
| 7,125,403 | B2 | 10/2006 | Julian et al. |
| 7,155,315 | B2 | 12/2006 | Niemeyer et al. |
| 7,239,940 | B2 | 7/2007 | Wang et al. |
| 7,306,597 | B2 | 12/2007 | Manzo |
| 7,607,440 | B2 | 10/2009 | Coste-Maniere et al. |
| 7,666,191 | B2 | 2/2010 | Orban, III et al. |
| 7,682,357 | B2 | 3/2010 | Ghodoussi et al. |
| 7,689,320 | B2 | 3/2010 | Prisco et al. |
| 7,695,481 | B2 | 4/2010 | Wang et al. |
| 7,695,485 | B2 | 4/2010 | Whitman et al. |
| 7,699,855 | B2 | 4/2010 | Anderson et al. |
| 7,713,263 | B2 | 5/2010 | Niemeyer |
| 7,725,214 | B2 | 5/2010 | Diolaiti |
| 7,727,244 | B2 | 6/2010 | Orban, III et al. |
| 7,741,802 | B2 | 6/2010 | Prisco et al. |
| 7,756,036 | B2 | 7/2010 | Druke et al. |
| 7,757,028 | B2 | 7/2010 | Druke et al. |
| 7,762,825 | B2 | 7/2010 | Burbank et al. |
| 7,778,733 | B2 | 8/2010 | Nowlin et al. |
| 7,803,151 | B2 | 9/2010 | Whitman |
| 7,806,891 | B2 | 10/2010 | Nowlin et al. |
| 7,819,859 | B2 | 10/2010 | Prisco et al. |
| 7,819,885 | B2 | 10/2010 | Cooper |
| 7,824,401 | B2 | 11/2010 | Manzo et al. |
| 7,835,823 | B2 | 11/2010 | Sillman et al. |
| 7,843,158 | B2 | 11/2010 | Prisco |
| 7,865,266 | B2 | 1/2011 | Moll et al. |
| 7,865,269 | B2 | 1/2011 | Prisco et al. |
| 7,886,743 | B2 | 2/2011 | Cooper et al. |
| 7,899,578 | B2 | 3/2011 | Prisco et al. |
| 7,907,166 | B2 | 3/2011 | Lamprecht et al. |
| 7,935,130 | B2 | 5/2011 | Williams |
| 7,963,913 | B2 | 6/2011 | Devengenzo et al. |
| 7,983,793 | B2 | 7/2011 | Toth et al. |
| 8,002,767 | B2 | 8/2011 | Sanchez et al. |
| 8,004,229 | B2 | 8/2011 | Nowlin et al. |
| 8,012,170 | B2 | 9/2011 | Whitman et al. |
| 8,054,752 | B2 | 11/2011 | Druke et al. |
| 8,062,288 | B2 | 11/2011 | Cooper et al. |
| 8,079,950 | B2 | 12/2011 | Stern et al. |
| 8,100,133 | B2 | 1/2012 | Mintz et al. |
| 8,108,072 | B2 | 1/2012 | Zhao et al. |
| 8,120,301 | B2 | 2/2012 | Goldberg et al. |
| 8,142,447 | B2 | 3/2012 | Cooper et al. |
| 8,147,503 | B2 | 4/2012 | Zhao et al. |
| 8,151,661 | B2 | 4/2012 | Schena et al. |
| 8,155,479 | B2 | 4/2012 | Hoffman et al. |
| 8,182,469 | B2 | 5/2012 | Anderson et al. |
| 8,202,278 | B2 | 6/2012 | Orban, III et al. |
| 8,206,406 | B2 | 6/2012 | Orban, III |
| 8,210,413 | B2 | 7/2012 | Whitman et al. |
| 8,216,250 | B2 | 7/2012 | Orban, III et al. |
| 8,220,468 | B2 | 7/2012 | Cooper et al. |
| 8,256,319 | B2 | 9/2012 | Cooper et al. |
| 8,285,517 | B2 | 10/2012 | Sillman et al. |
| 8,315,720 | B2 | 11/2012 | Mohr et al. |
| 8,335,590 | B2 | 12/2012 | Costa et al. |
| 8,347,757 | B2 | 1/2013 | Duval |
| 8,374,723 | B2 | 2/2013 | Zhao et al. |
| 8,528,440 | B2 | 3/2013 | Morley et al. |
| 8,418,073 | B2 | 4/2013 | Mohr et al. |
| 8,419,717 | B2 | 4/2013 | Diolaiti et al. |
| 8,423,182 | B2 | 4/2013 | Robinson et al. |
| 8,452,447 | B2 | 5/2013 | Nixon |
| 8,454,585 | B2 | 6/2013 | Whitman |
| 8,499,992 | B2 | 8/2013 | Whitman et al. |
| 8,508,173 | B2 | 8/2013 | Goldberg et al. |
| 8,529,582 | B2 | 9/2013 | Devengenzo et al. |
| 8,540,748 | B2 | 9/2013 | Murphy et al. |
| 8,551,116 | B2 | 10/2013 | Julian et al. |
| 8,562,594 | B2 | 10/2013 | Cooper et al. |
| 8,594,841 | B2 | 11/2013 | Zhao et al. |
| 8,597,182 | B2 | 12/2013 | Stein et al. |
| 8,597,280 | B2 | 12/2013 | Cooper et al. |

(56) References Cited

U.S. PATENT DOCUMENTS

| | | |
|---|---|---|
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart et al. |
| 8,989,903 B2 | 3/2015 | Weir et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,019,345 B2 | 4/2015 | Patrick |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,355,574 B2 | 5/2016 | Jian et al. |
| 9,393,017 B2 | 7/2016 | Flanagan et al. |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,788,907 B1 | 10/2017 | Alvi et al. |
| 9,795,446 B2 | 10/2017 | Dimaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 4/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,002,286 B1 | 6/2018 | Prabhu et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,147,052 B1 | 12/2018 | Lendvay et al. |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | Dimaio et al. |

(56) References Cited

U.S. PATENT DOCUMENTS

| | | |
|---|---|---|
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 11,205,508 B2 | 12/2021 | Venkataraman et al. |
| 2006/0084050 A1 | 4/2006 | Haluck |
| 2007/0136218 A1* | 6/2007 | Bauer .................. G16H 50/20 700/83 |
| 2008/0187896 A1 | 8/2008 | Savitsky |
| 2009/0177452 A1 | 7/2009 | Ullrich et al. |
| 2009/0311655 A1* | 12/2009 | Karkanias ............. G09B 5/065 434/262 |
| 2010/0167249 A1 | 7/2010 | Ryan |
| 2010/0241998 A1 | 9/2010 | Latta et al. |
| 2010/0248200 A1 | 9/2010 | Ladak et al. |
| 2013/0230837 A1 | 9/2013 | Meglan et al. |
| 2013/0295540 A1 | 11/2013 | Kesavadas et al. |
| 2014/0272866 A1 | 9/2014 | Kim |
| 2015/0248167 A1 | 9/2015 | Turbell |
| 2016/0133158 A1 | 5/2016 | Sui et al. |
| 2016/0182877 A1 | 6/2016 | Deluca |
| 2016/0378176 A1 | 12/2016 | Shiu |
| 2017/0116873 A1 | 4/2017 | Lendvay et al. |
| 2017/0140671 A1 | 5/2017 | Chui et al. |
| 2017/0220816 A1 | 8/2017 | Matusek et al. |
| 2017/0249432 A1 | 8/2017 | Grantcharov |
| 2017/0289623 A1* | 10/2017 | Bailey ................ H04N 21/4542 |
| 2017/0312031 A1 | 11/2017 | Amanatullah et al. |
| 2018/0005546 A1 | 1/2018 | Vazquez |
| 2019/0069957 A1 | 3/2019 | Barral et al. |
| 2019/0090954 A1* | 3/2019 | Kotian .................. H04N 23/90 |
| 2019/0133689 A1 | 5/2019 | Johnson et al. |
| 2019/0180083 A1 | 6/2019 | Gupta et al. |
| 2019/0279524 A1 | 9/2019 | Stoyanov et al. |
| 2019/0279765 A1 | 9/2019 | Giataganas et al. |
| 2020/0118677 A1 | 4/2020 | Giataganas et al. |
| 2020/0258616 A1 | 8/2020 | Likosky et al. |

OTHER PUBLICATIONS

Anonymous, "CyberGlove® II Wireless Data Glove: User Guide," CyberGlove Systems, 2009, 30 pages.

EP Search Report; Issued: Jul. 30, 2019; Application No. EP 19161135.9; Filed: Mar. 6, 2019; 10 pages.

3DSYSTEMS, "Doctors Practicing on Computers, Not Patients," URL: https://uk.3dsystems.com/learning-center/case-studies/doctors-practicing-computers-not-patients; Retrieved: Aug. 6, 2019; 6 pages.

3DSYSTEMS, "RobotiX Mentor," URL: https://simbionix.com/simulators/robotix-mentor; Retrieved: Aug. 6, 2019; 2 pages.

3DSYSTEMS, "Scanners and Haptics," URL: https://uk.3dsystems.com/scanners-haptics; Retrieved: Aug. 6, 2019; 6 pages.

Captoglove, "Virtual Reality & Smart Glove VR AR PC Mobile Gaming," URL: https://www.captoglove.com; Retrieved: Aug. 6, 2019; 8 pages.

Mimic Simulation, "FlexVR," URL: https://mimicsimulation.com/flexvr/; Retrieved: Aug. 6, 2019; 6 pages.

USENS, "Fingo," URL: https://usens.com/fingo; Retrieved: Aug. 6, 2019; 9 pages.

* cited by examiner

METHODS AND SYSTEMS FOR USING MULTIPLE DATA STRUCTURES TO PROCESS SURGICAL DATA

CROSS REFERENCE TO RELATED APPLICATIONS

This application is a continuation of U.S. application Ser. No. 16/292,108, filed Mar. 4, 2019, which claims the benefit of and priority to U.S. Provisional Application No. 62/639,349, filed Mar. 6, 2018, which is hereby incorporated by reference in its entirety for all purposes.

FIELD

The present disclosure generally relates to methods and systems for processing surgical data using multiple data structures for generating and/or updating an electronic output. More specifically, the present disclosure relates to using multiple interconnected data structures to process surgical data from one or more data streams of a surgical procedure that is represented by interconnected surgical maps that include precise and accurate descriptions of a surgical procedure. Additionally, the present disclosure relates to using a multi-dimensional artificial intelligence protocol to process surgical data from one or more data streams, using the multiple interconnected data structures, to identify a state in surgery, such that one or more detected characteristics can be compared to one or more target characteristics corresponding to the state of surgery to generate and/or update an electronic output.

BACKGROUND

Operational notes pertaining to the treatment and care of a patient during the course of a surgery are routinely prepared and compiled after a surgical procedure. Operational notes may include a variety of information including, for example, surgical actions, surgical tools, medical personnel, details of the procedures, or the results of the procedures and the complications, if any, which the patient experienced. Additionally, the content of an operational note may include observations, interpretations, and recommendations of a treating physician, a consulting physician, or other medical personnel. Operational notes are typically organized into sections, such as according to anatomy, pathology, and/or the content or subjects mentioned above.

However, there are a variety of disadvantages associated with the traditional approaches to preparing an operational note. For example, typically someone other than the author of the operational note prepares the transcript from the recording made by the physician. Discrepancies between the author's and physician's term definitions or background knowledge can then result in errors in the note that correspond to inaccurate and/or incomplete representations of events. Inaccuracies and/or data omissions can impact not only immediate patient care—particularly when the patient is in a critical condition—but also long-term healthcare costs. Highly variable, dynamic and/or unpredictable environments of a surgical procedure present challenges in terms of how representations of the environments are to be processed to output data to reliably generate and update operational notes.

BRIEF SUMMARY

In some embodiments, a computer-implemented method is provided. A surgical data set including surgical data collected during performance of a surgical procedure is obtained. The surgical data includes one or more data streams from the surgical procedure. A first surgical data structure that corresponds to the surgical dataset is identified. The first surgical data structure includes a plurality of nodes. Each node of the plurality of nodes represents a procedural state and a set of procedural metadata. Each node of the plurality of nodes are connected via at least one edge to at least one other node of the plurality of nodes. A second surgical data structure that corresponds to the surgical dataset is identified. The second surgical data structure includes a plurality of additional nodes. Each additional node of the plurality of nodes are connected via at least one edge to at least one other additional node of the plurality of additional nodes. Each additional node of the plurality of additional nodes are connected via at least one edge to at least one of the plurality of nodes of the first surgical data structure. A portion of the of the surgical dataset corresponding to a first node of the plurality of nodes from the first data structure and a corresponding second node of the plurality of additional nodes from the second data structure is determined based on the one or more data streams included in the portion. One or more edges are identified. Each edge of the one or more edges connect the first node of the first data structure to the second node of the second surgical data structure. Each edge of the one or more edges is associated with additional metadata corresponding to the surgical procedure. An edge of the one or more edges is selected based on the additional metadata associated with the one or more edges. Electronic data associated with the portion of the surgical dataset is generated based on the selected edge. Electronic data associating the electronic data with the portion of the surgical dataset is output.

In some embodiments, a computer-implemented method is provided. One or more data streams are received. Each data stream of the one or more data streams having been generated at and received from an electronic device configured and positioned to capture data during a surgical procedure. The one or more data streams including a set of information units. Each information unit of the set of information units corresponding to a different temporal association relative to other information units of the set of information units. Processing the one or more data streams using a multi-dimensional artificial-intelligence protocol based on the first data structure and the second data structure. The processing including repeatedly detecting new information units of the set of information units received as part of the one or more data streams and processing each data portion of the new information unit by: extracting features of the information unit to identify one or more features, wherein each of the one or more features corresponds to an incomplete subset of the data portion; classifying and/or localizing, for each of the one or more features and during a stage of the multi-dimensional artificial-intelligence protocol, the feature as corresponding to a particular object type of a set of predefined object types; determining, during the stage of the multi-dimensional artificial-intelligence protocol, a particular state of the set of procedural states based on the classifying and/or localizing and at least some of the metadata in the first data structure; identifying one or more properties corresponding to the one or more features; comparing the one or more properties to the metadata identified for the procedural state in the first data structure and the metadata identified for the second data structure; determining, based on the comparison and one or more predefined conditions and during another stage of the multi-dimensional artificial-intelligence protocol, whether a procedural departure occurred. A corresponding to a particular procedural instance is updated to include a file update corresponding to the information unit. The file update identifies the particular state, and the file update includes a representation of a result of at least part of the comparison when it is determined that a procedural departure occurred. The updated file is output.

In some embodiments, a computer-program product is provided that is tangibly embodied in a non-transitory machine-readable storage medium. The computer-program product can include instructions configured to cause one or more data processors to perform operations of part or all of one or more methods disclosed herein.

In some embodiments, a system is provided that includes one or more data processors and a non-transitory computer readable storage medium containing instructions which, when executed on the one or more data processors, cause the one or more data processors to perform operations of part or all of one or more methods disclosed herein.

BRIEF DESCRIPTION OF THE DRAWINGS

The present invention will be better understood in view of the following non-limiting figures, in which.

DETAILED DESCRIPTION

Figure 1:
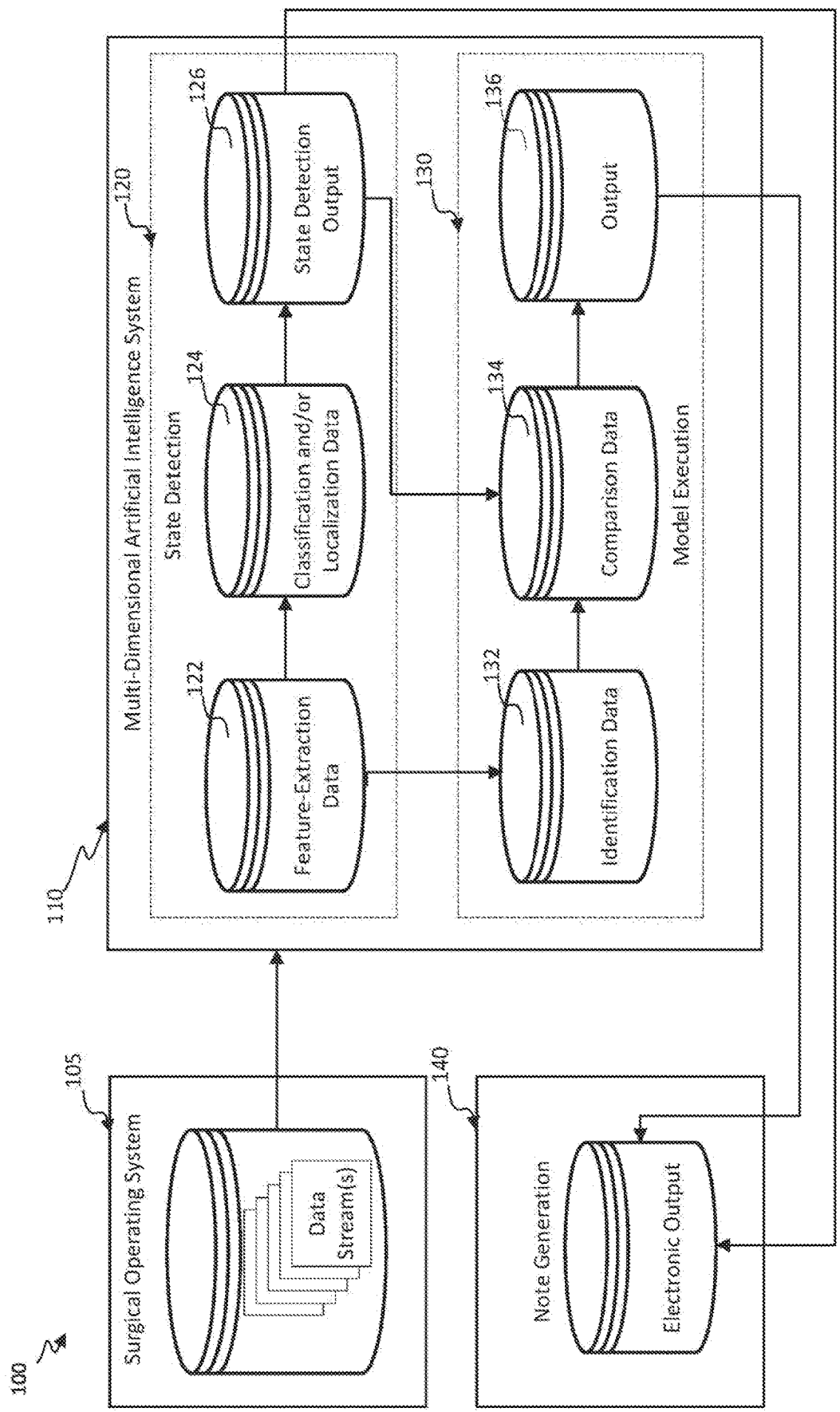
FIG. 1 shows a network for using data during a surgical procedure to identify procedural states and generate and/or update an electronic output in accordance with some embodiments of the invention.

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

In some embodiments, methods and systems are provided to process a surgical dataset, represented in multiple interconnected surgical data structures, which can be used to retrieve or generate pertinent information (e.g., corresponding to a surgical procedure) to generate (e.g., continuously update) an electronic output. The electronic output can be used to generate and/or update an operational note. Surgical data structures, that represent various characteristics in a surgery and corresponding information, can be locally retrieved or received. Each of the surgical data structures may include one or more connections between each respective surgical data structure (e.g., interconnected nodes) that represent characteristics in a surgery and corresponding information. The surgical dataset can be processed in accordance with the multiple interconnected surgical data structures associated with the surgery to identify characteristics of a surgical procedure (e.g., a specific procedural state, surgical tools, surgical actions, anatomical features, events, etc.). Metadata associated with the characteristics (e.g., which can include information associated with procedural state) can be retrieved (e.g., from the surgical data structure or from a location identified by the surgical data structure) and stored from each respective data structure to generate an electronic output. In some embodiments, the electronic output may be transmitted to a centralized hospital control center to provide additional information of the operating room conditions including (for example) procurement information (e.g., disposable equipment, sanitary items, tools, etc.).

Each of the surgical data structures of the multiple interconnected surgical data structures may include one or more nodes that are connected to nodes of another surgical data structure. The multiple interconnected surgical data structures may include more than two surgical data structures (e.g., more than three, more than four, more than five, etc.). The interconnected surgical data structures can include relational metadata (e.g., metadata associated with corresponding data structures) not available in a single data structure. For example, the interconnections between one or more surgical data structures can include relational metadata that identifies specific events during a surgical procedure. This relational metadata is unique to the connected surgical data structures. The metadata can be used to generate and/or update an electronic output (e.g., at a discrete time, at multiple times or continuously) during a surgical procedure or afterwards. The electronic output, based on the metadata, can identify (for example) a patient and one or more medical providers involved in a surgery, a type of surgery, an underlying condition, a result of the surgery, one or more states underwent throughout the surgery, a degree to which (e.g., for each of the one or more states) one or more observed properties matched one or more target properties for the state, one or more surgical tools used (e.g., and an association of individual states in which individual tools were used), and/or any departure from surgical targets.

Surgical data structures described herein may include intelligent system that collect and analyze operating room data and take actions that analyze the data through multiple interconnected data structures. Surgical data structures described herein may describe an appropriate surgical route using the surgical data structure and a number of inputs including one or more user inputs, operating room video or audio streams, smart surgical tools, accelerometer data from a surgeon or other operating room personnel, patient data, and medical records. Surgical data structures described herein determine the procedural location and a numerous other characteristics of the surgical procedure (e.g., surgical tools, anatomical features, spatial features, temporal information, etc.).

Each of the surgical data structures may also function independently. In some cases, each of the surgical data structures can independently process the one or data streams from the surgical procedure. For example, a first data structure can identify procedural stages of a surgical procedure, a second data structure can identify surgical tools in a surgical procedure, and a third data structure can identify surgical actions in a surgical procedure. In portions of the surgical procedure that do not include a surgical tool, the one or more data streams can be processed using the first data structure to identify the stage of surgery. Alternatively, the one or more data streams can be processed using the second data structure to identify the events during a surgical procedure. In this instance, the electronic output may only relate to one of the surgical data structures or a combination of data structures (e.g., first and third data structure, first and second data structure, second and third data structure, etc.).

In some embodiments, the surgical data can be processed in accordance with multiple surgical data structures associated with the surgery to identify characteristics of the surgical procedure (e.g., specific procedural state, surgical actions, surgical tools, or risk). Procedural metadata associated with the surgical procedure can be retrieved (e.g., from the surgical data structure or from a location identified by the surgical data structure) from each surgical data structure, a corresponding interrelation (e.g., metadata associated with each surgical data structure) can be identified between each surgical data structure, and transmitted.

In some embodiments, each of the surgical data structures can be generated using data streams obtained from previous surgical procedures. In one instance, video streams from a previous surgical procedure can be processed (e.g., using image-segmentation) to identify, detect, and determine probabilities of a surgical procedure. The video streams can be annotated to include information relevant to different portions of the surgical procedure to generate surgical data structures. For example, a video stream from an endoscopic procedure can be segmented to identify surgical instruments during the procedure. The surgical data structure can be generated by using training data with pixel-level labels (i.e., full supervision) from the segmented endoscopic procedure video stream. In some aspects, generating a surgical data structure can be produced using other methods. For example, a video stream from an endoscopic procedure can be processed to detect instruments by using three different processes: identification (e.g., identifying which instrument is present in the image), bounding box regression (e.g., localizing each instrument in the image by finding a bounding box that encloses them), and heatmap regression (e.g., probability maps of where instruments might be present). This information can be compiled to generate a surgical data structure.

Each of the surgical data structures may include a plurality of nodes and a plurality of edges. Each edge of the plurality of edges may be configured to connect two nodes of the plurality of nodes. The nodes and edges may be associated with and/or arranged in an order that corresponds to a sequence in which various actions may be performed and/or specific surgical instruments in a surgical procedure. Each of one more or all nodes in the surgical data structure and/or each of one, more or all edges in the surgical data structure may be associated with surgical metadata In some embodiments, each surgical data structure can include multiple nodes, each node representing particular characteristics of surgery (e.g., procedural state, state of a patient, surgical instruments, etc.). For example, in one data structure, a node can represent a discrete physiological and procedural state of the patient during a procedure (e.g., initial preparation and sterilization complete, skin incision made, bone exposed, etc.) and, in a second data structure, a node can represent a discrete surgical tool in the operating room during a procedure (e.g., forceps, stapler, laparoscopic instruments, etc.). The nodes of the first data structure and the nodes of the second data structure can be interconnected to provide relational metadata. For example, the relational metadata may represent a pose, anatomical state, sterility, a state of a patient, such as patient position, location of an organ, location of a surgical instrument, location of an incision, etc.

Each surgical data structure can further include multiple edges, with each edge connecting multiple nodes and representing a characteristic of a surgical procedure. Each edge of the plurality of edges may be configured to connect two nodes of the plurality of nodes. The nodes and edges may be associated with and/or arranged in an order that corresponds to a sequence in which various actions may be performed in a surgical procedure. Each of one more or all nodes in the surgical data structure and/or each of one, more or all edges in the surgical data structure may be associated with procedural metadata. In some cases, an edge that connects two nodes of the plurality of nodes within a single data structure can represent transition within that specific data structure. For example, for a data structure representing procedural states, an edge can represent one or more surgical actions executed to transition between different nodes. In other embodiments, an edge can connect two nodes of the plurality of nodes between two different data structures. Each the edges connecting interconnecting nodes between surgical data structures may be associated with additional procedural metadata. Each edge can be associated with information about the surgical action, such as an identification of the action, a time typically associated with the action, tools used for the action, a position of interactions relative to anatomy, etc. For example, for an interconnected set of nodes between two data structures can pool metadata from each respective data structure to represent additional characteristics of a surgical procedure.

For example, a first data structure can include multiple nodes, each node representing a procedural state, and a second data structure can include multiple nodes, each node representing a surgical instrument. The multiple nodes from the first data structure can be connected (e.g., via edges) to the multiple nodes of the second data structure. The edges interconnecting the nodes of each structure may include information included in or identified by relational metadata. The edges between nodes for each data structure may (for example) identify the procedural state (e.g., by identifying a state of a patient, progress of a surgery, etc.), identify an action that is being performed or is about to be performed (e.g., as identified in an edge that connects a node corresponding to the procedural state with a node corresponding to a next procedural state), and/or identify one or more considerations (e.g., a risk, tools being used or that are about to be used, a warning, etc.).

In one embodiment, the one or more data streams are processed by each of the data structures (for example) to identify a procedural state, identify one or more surgical tools in the procedural state, and one or more surgical actions in the surgical procedure. For example, one data structure may identify surgical actions represented in a surgical data structure and another data structure may identify surgical tools used in a stage of surgery. Each of the data structures can include multiple nodes that are connected by edges across surgical data structures. Based on the identified nodes and related edges, (relational) metadata is availed. The metadata can provide information regarding events that occurred during a procedure (for example) including surgical events, risk assessment, or detection of actions that lead to specific events. For example, based on the identified state, the data structures can identify the spatial relation of a surgical tool to an anatomical feature over a period of time that may have caused damage or bleeding. This information can be an electronic output. The electronic output can be stored as an operational note.

In some instances, a computer-implemented method is provided that uses a multi-dimensional artificial intelligence to process live or previously collected surgical data. The processing, using the multiple interconnected structures, can result in both an identification of particular characteristics of the surgery and further a comparison of the particular characteristics to target characteristics. Information can be selected based on the comparison to generate or update an electronic output. More specifically, surgical data can be received from one or more data streams. Each of multiple epochs of the surgical data can be processed to identify a procedural state in surgery. For example, each of the multiple epochs can correspond to a time interval (e.g., such that a state is identified for each 20-second interval of the surgical data). Thus, in some instances, a same state may be identified for multiple consecutive epochs. Identifying one or more epochs of data can include (for example) dividing or parsing continuous data and/or assigning individual non-continuous (e.g., discrete or semi-continuous) data sets and/or non-continuous data points to individual epochs. For example, a single data point (e.g., representing movement of a particular surgical tool) can be associated with a time identified in a same communication that included the single data point or with a time at which the single data point was received, and the single data point can then be assigned to an epoch corresponding to a time window that includes the time. Data assigned to a given epoch can then be processed to identify to which state (from amongst multiple predefined states) the epoch corresponds.

The state can be determined using a first data structure (e.g., procedural-state data structure) that indicates, for each of the multiple predefined states, a set of state characteristics of the state. The set of state characteristics can include (for example) one or more required characteristics (that are definitively and reliably true for the state), one or more possible characteristics (that may be true for the state) and/or one or more exclusion characteristics (that cannot be true for the state). It will be appreciated that, in some instances, a state may still be identified despite a lack of detecting a required characteristic. This situation may occur when the required characteristic is unreliably detectable. Thus, the first structure may be configured to be evaluated based on one or more (e.g., predefined or learned) probabilities. A probability may indicate a likelihood of detecting a given characteristic or a probability that a possible characteristic is an actual characteristic of the state. Using detected data and the characteristics (and potentially the probabilities) of the data structure, a score can be determined for each epoch and each state, and a state having a highest score for a given epoch can be assigned to the epoch.

The data structure can also include order constraints and/or order probabilities, which can indicate (for example) a possibility and/or likelihood of transitioning from one state to another state. This order data can be used to constrain states considered for assignment for a given epoch based on a state assignment from one or more previous epochs. Further, the order data can be used to (for example) weight, bias or inform a state assignment. Additional detail of data structures to be used for state assignment can be found in U.S. Pat. No. 9,788,907, filed on Feb. 20, 2017, which is hereby incorporated by reference in its entirety for all purposes.

The surgical data assigned to an epoch can be used not only to identify a particular state that corresponds to the data epoch but also (or alternatively) to characterize particular actions, events or other characteristics of the epoch, according to a second data structure. For example, each of the data structures can be used to detect and/or classify (or localize) an object in an epoch, identify one or more properties of the object (e.g., Cartesian position, angular position, movement direction and/or operation type) and compare the object type and/or one or more properties to one or more corresponding target parameters defined for the state.

The detected data, inferred information and/or comparison results can be used to facilitate provision of feedback (e.g., at a discrete time, at multiple times or continuously) during a surgical procedure or afterwards. In some instances, the feedback is provided in an electronic output. The electronic output can identify (for example) a patient and one or more medical providers involved in a surgery, a type of surgery, an underlying condition, a result of the surgery, one or more states underwent throughout the surgery, a degree to which (e.g., for each of the one or more states) one or more observed properties matched one or more target properties for the state, one or more surgical tools used (e.g., and an association of individual states in which individual tools were used), and/or any departure from surgical targets. The electronic output can be used to generate one or more user-level reports (e.g., corresponding to a particular medical professional) and/or one or more management-level reports (e.g., corresponding to a medical team and/or institution). For example, the electronic output can be availed to a device of a decision maker (e.g., a surgeon) and/or a group or panel of reviewers, such that real-time decisions or high-level approaches can be adjusted.

In some cases, a plurality of sensors (e.g., cameras, microphones, or medical equipment) can capture one or more data streams during a surgical operation. It will be appreciated that, as used herein, a data stream may correspond to data that is continuously transmitted from a source to a target over a time window, data that is intermittently (e.g., periodically or upon-detection) transmitted from a source to a target over a time window, a discrete transmission from a source to a target and/or multiple discrete transmissions. For example, a data stream may include a video feed of a surgery, a set of regularly spaced and discrete vital-sign measurements, discrete detection events indicating times in which a particular surgical tool was activated, a set of controlled video feeds with start and end times occurring within a total surgical time and being controlled by a user, etc.

The one or more data streams may be transmitted (e.g., as it is collected or after collection of all data from a procedure) to a processing unit that may process the data in real-time or store the data for subsequent processing. The one or more data streams can be processed using a multi-dimensional artificial intelligence in order to automatically generate or update an electronic output associated with a particular surgery and/or an electronic medical record (EMR) associated with a particular patient. The note or record can be generated or updated to include a report of multiple observations detected in association with during a surgical procedure including (for example) instruments used during the surgical procedure (e.g., and/or states in which the instruments were used and/or manners in which the instruments were used), particular steps completed (e.g., in association with particular states), and/or error information (e.g., reflecting discrepancies between observed characteristics and target characteristics, such as detecting that a stapler or clip was not used during a particular state). Target characteristics can be defined to (for example) correspond to high or optimal action precision, ergonomic optimization, action efficacy and/or patient safety.

One or more types of artificial-intelligence techniques can be used to process the surgical data to detect and identify objects of relevance within the surgical data. For example, multiple interconnected data structures as described herein can be used to process the surgical data to detect and identify objects of relevance. A data structure (e.g., a procedural-state data structure) associated with a set of procedural states for a surgical procedure can include a set of characteristic procedural metadata associated with each procedural state from a set of procedural states. The multi-dimensional artificial intelligence, in one stage, can process input data to (for example) detect particular characteristics of the data. In some instances, the detection is performed at an epoch level, such that input data is assigned to individual epochs and then input data for each epoch is processed to identify one or more particular characteristics for the epoch. For example, the processing may include extracting features from a video data to identify discrete objects (and/or discrete tool usages and/or actions) and classifying and/or localizing each object (and/or tool usage and/or action). The multi-dimensional artificial intelligence, in another stage, can compare the one or more characteristics to the one or more target characteristic metadata identified for the procedural state in the multiple interconnected data structures to determine whether, an extent to which and/or a type of a procedural departure occurred.

The one or more data streams can be generated and received from one or more electronic devices configured and positioned to capture live or previously collected data during a surgical procedure. The one or more data streams can include (for example) time-varying image data (e.g., a video stream from different types of cameras), audio data (e.g., instructions from medical personnel, for example, a surgeon), and/or electrical signals (e.g., data from equipment in surgical procedure). The data streams may vary depending on the type of operation. For example, which types of data streams are received may depend on a type of surgery (for example) including open surgery techniques, laparoscopic surgery techniques, or microscopic surgery techniques. Generally, some data streams available during a surgical procedure (for example) can include video data (e.g., in-light camera, laparoscopic camera, wearable camera, microscope, etc.), audio data (e.g., near-field sounds, far-field sounds, microphones, wearable microphones, etc.), signals from medical devices (e.g., anesthesia machine, pulse and blood pressure monitors, cardiac monitors, navigation systems, etc.) and/or various inputs from other operating room equipment (e.g., pedals, touch screens, etc.). Using one or more data streams, the methods and systems can identify progression through various surgical states and/or compare actual observed events throughout the surgery to target or expected results (e.g., for the surgery and/or individual states). This assessment (and/or a processed version thereof) can be identified in a generation or update of an electronic output (e.g., an operational note and/or an electronic medical record).

The multi-dimensional artificial intelligence can be used to process (e.g., in real-time or offline) one or more data streams (e.g., video streams, audio streams, RFID data, etc.). The processing can include (for example) detecting and characterizing one or more features within various instantaneous or block time periods. Each feature can be detected (for example) using feature extraction and can be classified and/or localized (e.g., finding the position of a specific feature). The feature(s) can then be used to identify a presence, position and/or use of one or more objects, characterize a representation of each object (e.g., in terms of its orientation, position, use state, movement characteristic, etc.), which can be used (e.g., in combination with other object detections and/or characterizations) to identify a state within a workflow (e.g., as represented via a surgical data structure), compare one or more properties (e.g., orientation, position, and/or movement) of the one or more identified features to one or more target properties for the state, etc.).

Techniques described herein can facilitate various technical advantages. In some instances, more efficient data storage and/or more efficient querying can be facilitated by identifying data properties and target discrepancies that can more efficiently represent complex and extended data from multiple sources. Further, identifying, storing and communicating data and results in association with procedural states increases the relevance of the data, which can thus result in storage and procedural efficiencies. For example, the state-based approach can facilitate efficient implementation of a query to identify a state within a particular procedure in which a prevalence of deviation between target characteristics and actual characteristics was maximized across states of the procedure. As another example, the state-based approach can facilitate efficient querying to detect a distribution across possible action implementations corresponding to a given state in the procedure. As yet another example, the state-based approach can facilitate identifying a prominent predictor of an early-state action on a later-state result. Each of these queries may have been difficult to impossible if surgical data was stored in a non-state-based manner.

FIG. 1 shows a network for using live or previously collected data from a surgical procedure to generate and/or update an electronic output in accordance with some embodiments of the invention. Network 100 includes a surgical operating system 105 that collects one or more data streams from a surgical procedure. Surgical operating system 105 can include (for example) one or more devices (e.g., one or more user devices and/or servers) located within and/or associated with a surgical operating room and/or control center. Network 100 further includes a multi-dimensional artificial intelligence system 110 that processes the one or more data streams to identify a procedural state, to determine one or more properties of the actual data (e.g., in relation to the procedural state) and to compare the one or more properties to one or more target properties for the procedural state, which is used to generate a corresponding output. In some embodiments, network 100 can also process the one or more data streams, using the multi-dimensional artificial intelligence system 110, to anonymize (e.g., distort, blur, or color) the one or more data streams. For example, the network 100 can store the data so as to anonymize the data and/or to obscure and/or encrypt particular (e.g., private or identifying) features. In some embodiments, surgical data (or a processed version thereof, such as timestamped state identification) can be preserved for anonymization. It will be appreciated that the multi-dimensional artificial intelligence system 110 can include one or more devices (e.g., one or more servers), each of which can be configured to include part or all of one or more of the depicted components of multi-dimensional artificial intelligence system 110. In some instances, part or all of multi-dimensional artificial intelligence system 110 is in the cloud and/or remote from an operating room and/or physical location corresponding to part or all of surgical operating system 105.

Surgical operating system 105 can include (for example) one or more devices (e.g., one or more user devices and/or servers) located within and/or associated with a surgical operating room and/or control center. In some embodiments, the surgical data from the surgical operating system 105 can include digital video data, which may include a continuous signal that represents moving visual images. The surgical data may (e.g., alternatively or additionally) include audio data, representations of one or more inputs received at a device (e.g., a voice command, a motion command or input received at a keyboard or other interface component), data from a smart surgical tool (e.g., indicative of a location, movement and/or usage), and so on. The surgical data can include data collected from a single device or from multiple devices. The surgical data can include data collected over a time period (e.g., a predefined time increment, since a previous state-transition time or procedure initiation time, or a time of an entire surgical procedure). The surgical data may include raw data collected during the surgery or a processed version thereof (e.g., to reduce noise and/or transform a signal, such as transforming accelerometer data collected at a headset to a movement command indicating that the surgical procedure has progressed to a next step).

Multi-dimensional artificial intelligence system 110 can access a data structure. The data structure can be associated with a set of procedural states for a surgical procedure. The data structure can identify characteristics for each procedural state of the set of procedural states. Each procedural state may be associated with a set of characteristic procedural metadata that indicates one or more data characteristics that correspond to the procedural state and one or more target characteristic metadata. Metadata and target characteristic metadata can identify (for example) particular tools, anatomic objects, medical personnel, actions being performed in the instance, and/or surgical states. Multi-dimensional artificial intelligence system 110 can use the corresponding metadata and/or target characteristic metadata to define one or more parameters of the model so as to learn (for example) how to transform new data to identify features of the type indicated by the metadata and/or target characteristic metadata.

In some embodiments, the data structure may be received from another remote device (e.g., cloud server), stored and then retrieved prior to or during performance of a surgical procedure. The data structure can provide precise and accurate coded descriptions of complete surgical procedures. The data structure can describe routes through surgical procedures. For example, the data structure can include multiple nodes, each node representing a procedural state (e.g., corresponding to a state of surgery). The data structure can further include multiple edges, with each edge connecting multiple nodes and representing a surgical action.

In some instances, multi-dimensional artificial intelligence system 110 can access a data structure and accordingly configure an artificial intelligence system. The artificial intelligence system can include, for example, a machine-learning model trained using the surgical data structure. The trained machine-learning model can include, for example, a convolutional neural network adaptations, adversarial networks, recurrent neural networks, deep Bayesian neural networks, or other type of deep learning or graphical models.

Multi-dimensional artificial intelligence system 110 can process the one or more data streams from the surgical operating system 105. In a first stage, multi-dimensional artificial intelligence system 110 can process the one or more data streams to perform state detection 120. For state detection 120, a procedural state is determined from the one or more data streams. The one or more data streams may include a set of information units. Each information unit of the set of information units may correspond to a different temporal association relative to other information units of the set of information units. Multi-dimensional artificial intelligence system 110 can repeatedly detect new information units of the set of information units received as part of the one or more data streams and process each data portion of the new information unit.

During state detection 120, the multi-dimensional artificial intelligence system 110 can generate feature-extraction data 122 by feature extraction or localization (e.g., segmenting) each data portion of the new information unit to identify one or more features. Each of the one or more features of the feature-extraction data may correspond to an incomplete subset of the data portion. For example, the new information unit can correspond to an incomplete subset of time-varying image data (e.g., a video stream from different types of cameras), such as a set of pixels. The multi-dimensional artificial intelligence can extract features from the time-varying image data to identify and/or characterize each of the one or more objects (e.g., medical personnel, tools, anatomical objects) that are depicted in the image or video. The characterization can (for example) indicate a position of the object in the object (e.g., a set of pixels that correspond to the object and/or a state of the object that is a result of a past or current user handling). Metadata and feature-extraction data can identify (for example) particular tools, anatomic objects, actions being performed in the simulated instance, and/or surgical states.

Multi-dimensional artificial intelligence system 110 can perform a classification and/or localization of the feature-extraction data 122 to obtain classification and/or localization data 124. For example, the multi-dimensional artificial intelligence system 110 can classify the feature-extraction data 122 as corresponding to a particular object type of a set of predefined object types in a classification 124 during state detection 120. The artificial intelligence can determine (e.g., state-detection stage) a particular state based on the classification and at least some of the sets of characteristic procedural metadata in the data structure. In some instances, the multi-dimensional artificial intelligence system can be configured to classify an image using a single image-level classification or by initially classifying individual image patches. The classifications of the patches can be aggregated and processed to identify a final classification.

The state detection 120 can use the output from the classification and/or localization to determine a particular state of a set of procedural states based on the classification and/or localization data 124 and at least some of the sets of characteristic metadata in the data structure. For example, information from the data structure can identify a set of potential states that can correspond to part of a performance of a specific type of procedure. Different procedural data structures (e.g., and different machine-learning-model parameters and/or hyperparameters) may be associated with different types of procedures. The data structure can include a set of nodes, with each node corresponding to a potential state. The data structure can include directional connections between nodes that indicate (via the direction) an expected order during which the states will be encountered throughout an iteration of the procedure. The data structure may include one or more branching nodes that feeds to multiple next nodes and/or can include one or more points of divergence and/or convergence between the nodes. In some instances, a procedural state indicates a procedural action (e.g., surgical action) that is being performed or has been performed and/or indicates a combination of actions that have been performed. In some instances, a procedural state relates to a biological state of a patient.

Each node within the data structure of the multiple interconnected data structures can identify one or more characteristics of the state. The characteristics can include visual characteristics. In some instances, the node identifies one or more tools that are typically in use or availed for use (e.g., on a tool tray) during the state, one or more roles of people who are performing typically performing a surgical task, a typical type of movement (e.g., of a hand or tool), etc. Thus, state detection 450 can use the feature-extraction data 122 generated by multi-dimensional artificial intelligence system 110 (e.g., that indicates the presence and/or characteristics of particular objects within a field of view) to identify an estimated node to which the real image data corresponds. Each of the surgical data structures may include one or more interconnected nodes between each respective surgical data structure (e.g., interconnected nodes) that represent metadata (e.g., characteristics) in a surgical procedure and corresponding information. Identification of the node(s) (and/or state) can further be based upon previously detected states for a given procedural iteration and/or other detected input (e.g., verbal audio data that includes person-to-person requests or comments, explicit identifications of a current or past state, information requests, etc.) from multiple interconnected data structures.

Multi-dimensional artificial intelligence system 110 can include a model execution 130. During model expectation 130, the multi-dimensional artificial intelligence system 110 processes the feature-extraction data 122 to determine identification data 132. The multi-dimensional artificial intelligence system 110 identifies one or more properties corresponding to the one or more features. For example, the one or more properties may identify one or more sets of characteristics for the one or more features. An identification is made as to which characteristics are to be specifically fixed and/or varied (e.g., in a predefined manner). The identification can be made based on (for example) input from a client device, a distribution of one or more characteristics across the base images and/or videos and/or a distribution of one or more characteristics across other real image data.

Using the identification data 132 in the one or more extracted features, the model execution 130 generates comparison data 134 for each of the one more features. The multi-dimensional artificial intelligence may generate the comparison data 134 by comparing the one or more properties to the one or more target characteristic metadata identified for the procedural state in the data structure. In some instances, the model execution system includes or is associated with a preprocessing (e.g., intensity normalization, resizing, etc.) that is performed prior to extracting features from the image(s). An output of the execution system can include feature extraction data that indicates which (if any) of a defined set of objects are detected within the image data, a location and/or position of the object(s) within the image data, and/or state of the object. Based on the comparison and one or more predefined conditions during another stage of the multi-dimensional artificial-intelligence protocol, the model execution outputs whether a procedural departure occurred.

The state detection output 126 and the model execution output 130 can be transmitted to note generation 140. The note generation 140 can use the state detection output 126 to identify the particular state of surgery. The note generation 140 can then use the state detection output 136 to update a file. The output generation for each stage of the multi-dimensional artificial intelligence can generate and/or retrieve information associated with the state and/or potential next events. For example, the information can include details as to warnings and/or advice corresponding to current or anticipated procedural actions. The information can further include one or more events for which to monitor. The information can identify a next recommended action.

Figure 2:
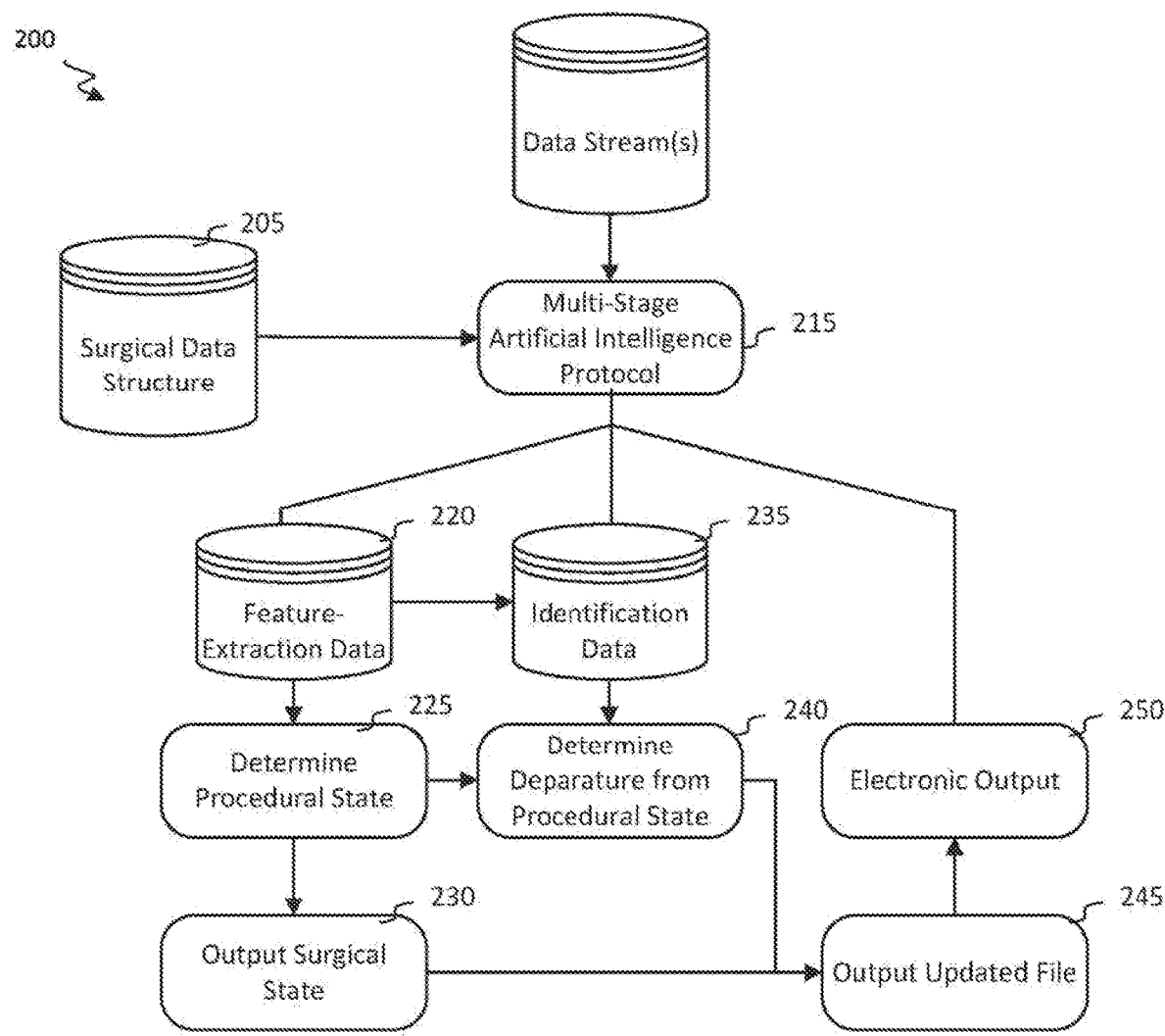
FIG. 2 shows a network for identifying procedural states in accordance with some embodiments of the invention.

FIG. 2 shows a data-processing flow 200 for processing live or previously collected surgical data in accordance with some embodiments of the invention. In some embodiments, systems and methods used to process data to identify a real-time state of a surgery, represented in a surgical data structure, which can be used to generate an updated file based on a comparison with one or more data streams from a data stream (e.g., corresponding to a current or subsequent action). Initially, the process may access a surgical data structure 205. For example, the surgical data structure may be received from another remote device (e.g., cloud server), stored and then retrieved prior to or during performance of a surgical procedure. The surgical data structure can provide precise and accurate coded descriptions of complete surgical procedures. The surgical data structure 205 can describe routes through surgical procedures. For example, the surgical data structure 205 can include multiple nodes, each node representing a procedural state (e.g., corresponding to a state of a patient).

In some embodiments, the surgical data structure 205 can be associated with a set of procedural states for a surgical procedure. The set of set of procedural states can identify, for each procedural state of the set of procedural states, a set of characteristic procedural metadata that indicates one or more data characteristics that correspond to the procedural state and one or more target characteristic metadata. The metadata and/or target characteristic metadata can identify (for example) particular tools, anatomic objects, actions being performed in the simulated instance, and/or surgical states.

During a surgery, live or previously collected surgical data 210 can be collected (e.g., from a sensor at a wearable device, smart surgical instrument, etc.). The surgical data 210 may include one or more data streams including a set of information units. Each information unit of the set of information units corresponds to a different temporal association relative to other information units of the set of information units. For example, one or more data streams from a surgical procedure can be collected from one or more cameras, one or more microphones, or one or more electrical signals (e.g., from medical equipment). The surgical data 210 may include (for example) user inputs, a video stream, or operating room data. For example, user inputs may include manual inputs directly provided by operating room personnel (e.g., via a wearable device or non-wearable device located inside or near an operating room). For example, operating room personnel may include the performing surgeon, a nurse, an anesthetist, or remote surgeon watching the procedure. Inputs may include gesture, voice, another form of hands-free sterile interaction and even direct contact with a computer user-interface. As another (additional or alternative) illustration, surgical images may be recorded, such as those captured on video from a head-mounted surgeon camera. As yet another (additional or alternative) illustration, surgical data may include other operating room data such as; time elapsed in procedure, nodes already passed by the users (e.g., surgeon, nurse or team member), identified surgical instruments used or in use, personnel present in the operating room and user movements measured from accelerometers in a guidance system headset or other system-connected wearable devices.

A multi-dimensional artificial intelligence protocol 215 can receive the surgical data 210. The multi-dimensional artificial intelligence protocol 215 segments the surgical data 210 into one or more segments to generate feature-extraction data 220 for each data stream of the surgical data. The one or more segments correspond to an incomplete subset of the data portion. In some embodiments, the artificial intelligence segments the surgical data 210 using feature extraction. Anatomic feature extraction can be performed on the surgical images to detect an anatomic state, anatomic pose, or any other attribute possible to derive from video that can be used later to determine a precise procedural state. Additional data such as user input or operating room data may assist with feature extraction. The feature extraction algorithm used to detect a one or more properties from the surgical data may include machine learning iterations. In particular, if the first implementation of the systems and methods described herein requires manual navigation through the procedure by the user (e.g., surgeon, nurse or team member), the resulting dataset of live or previously collected surgical images and associated navigation commands can be used as an effective algorithm training resource using machine learning software. In other embodiments, a component may be associated with a user input or operating room data.

In a first stage, a multi-dimensional artificial intelligence can identify the current procedural state 225 from the feature-extraction data 220. Based on each of the one or more segments from the feature-extraction data 220, each segment can be classified and/or localized as corresponding to a particular object type of a set of predefined object types. The multi-dimensional artificial-intelligence protocol can determine a particular state 225 of the set of procedural states based on the classification and/or localization and at least some of the sets of characteristic procedural metadata in the data structure.

In some embodiments, temporal information is identified for a part of the data streams associated with the procedural state. The temporal information may include (for example) a start time, end time, duration and/or range. The temporal information may be absolute (e.g., specifying one or more absolute times) or relative (e.g., specifying a time from a beginning of a surgery, from a beginning of a procedure initiation, etc.). The temporal information may include information defining a time period or time corresponding to the video data during which it is estimated that the surgery was in the procedural state.

The temporal information may be determined (for example) based on information associated with the state identification. For example, if surgery data is divided into data chunks, and each data chunk is associated with a procedural state, the temporal information may identify a start and end time that corresponds to (for example) a start time of a first data chunk associated with a given procedural state and an end time of a last data chunk associated with a given procedural state, respectively. As another example, if discrete data points are received that are indicative of state transitions, the temporal information may include times associated with two consecutive data points. As yet another example, a data set may be analyzed to detect state transitions (e.g., by detecting activation/inactivation of a particular smart tool, detecting a time period during which a particular visual characteristic is detected in video data, detecting times at which an audio command is detected in an audio signal that indicates that a state is transitioning, etc.).

It will be appreciated that transitions between different states may have a same or different transition characteristic.

The multi-dimensional artificial intelligence can output 230 the identified procedural state. In some embodiments, the output 230 of the identified procedural state can include (for example) feature-extraction data (e.g., that indicates which object(s) are present within the image data and/or corresponding position information) and/or an identification of a (current and/or predicted next) procedural state. If the output does not identify a procedural state, the output may be further processed (e.g., based on procedural-state definitions and/or characterizations as indicated in a data structure) to identify a (current and/or predicted next) state.

In a second stage, the multi-dimensional artificial intelligence can generate identification data 235. The identification data 235 identifies one or more properties corresponding to the feature-extraction data 220. For example, the one or more properties identified in the feature-extraction data 220 can include one or more objects (e.g., medical personnel, tools, anatomical objects) that are depicted in an image or video. The multi-dimensional artificial intelligence can compare the identification data 235 corresponding to the feature-extraction data with the one or more target characteristic metadata identified for the procedural state in the data structure. Based on the comparison and one or more predefined conditions, the multi-dimensional artificial intelligence can determine whether a procedural departure occurred 240.

An output of an updated file 245 indicating the departure from the procedural state is generated based on the identified state. The output 245 can include (for example) information and/or recommendations generally about a current state, information and/or recommendations based on live data and the current state (e.g., indicating an extent to which a target action associated with the state is being properly performed or identifying any recommended corrective measures), and/or information and/or recommendations corresponding to a next action and/or next recommended state. The output 245 can be availed to update an electronic output 250. For example, the electronic output 250 can be transmitted to a user device within a procedure room or control center.

The electronic output 250 may be transmitted (e.g., in association with an identifier of the video data or surgical procedure) to storage or another device. In some instances, the temporal information is used to annotate and/or assess video data. For example, it may be determined whether a surgical team traversed through an approved set of actions. As another example, a video may be annotated with captions to identify what steps are being performed (e.g., to train another entity).

Figure 3:
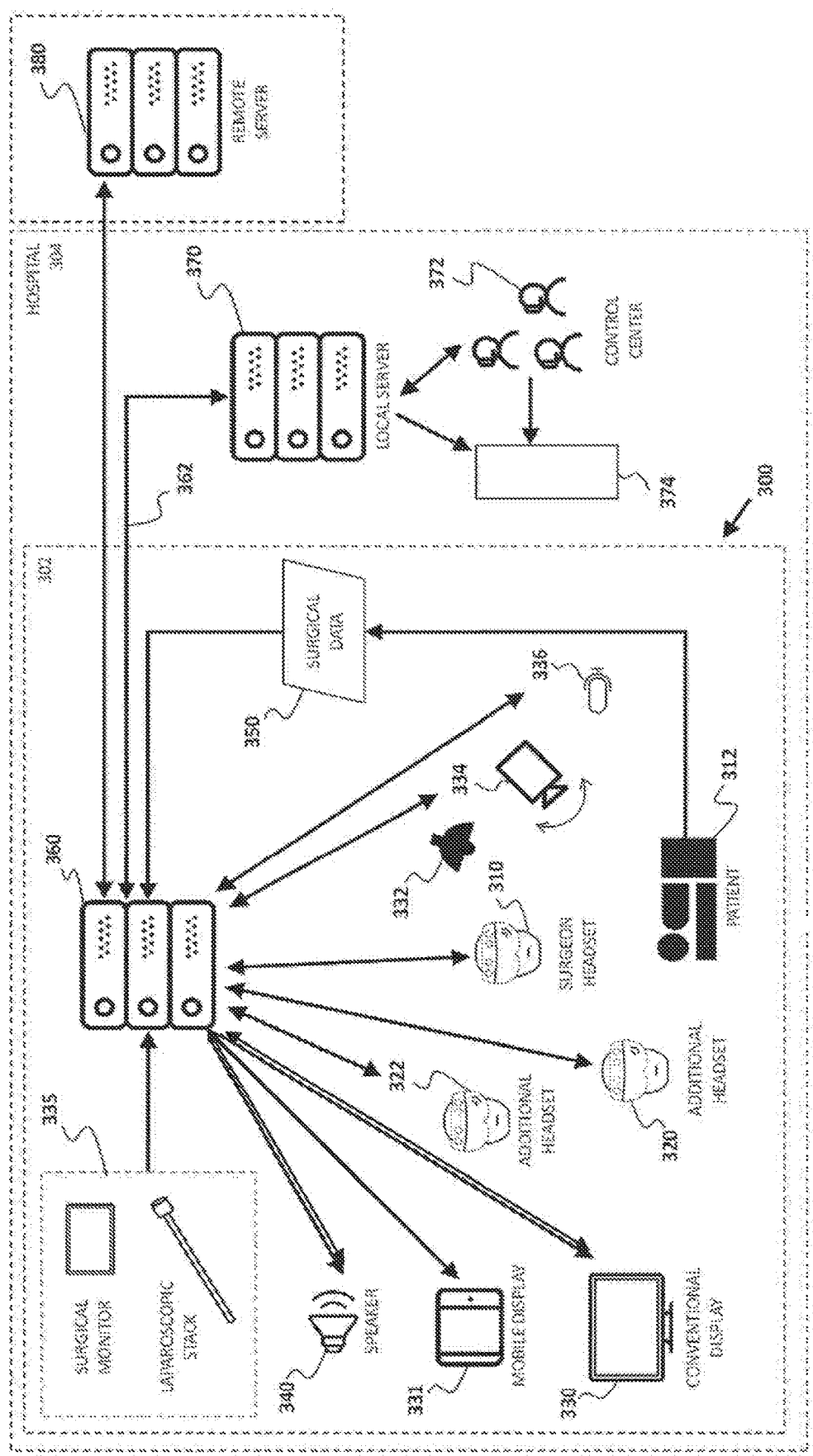
FIG. 3 shows an embodiment of a system for collecting data and producing an electronic output in accordance with some embodiments of the invention.

FIG. 3 shows an embodiment of a system 300 for collecting live or previously collected data and/or presenting data corresponding to state detection, object detection and/or object characterization performed based on executing a multi-dimensional artificial intelligence. System 300 can include one or more components of a procedural control system.

Computing device 360 can be placed inside the operating room or worn by a member of the operating room (e.g., surgeon, medical assistant, nurse, etc.) to capture data steams (e.g., video content) of the surgical environment. The data can include image data (which can, in some instances, include video data) and/or other types of data. For example, in laparoscopic or microsurgery procedures, computing device 360 may capture video data streams from video sources, such as a laparoscopic stack or a surgical monitor (collectively, 335), with video outputs. The data can be transmitted to a computing device 360 via a wired connection or a wireless connection. In some embodiments, the computing device 360 may be wirelessly connected. The computing device 360 can collect data from a number of sources including (for example) a surgeon mounted headset 310, a first additional headset 320, a second additional headset 322, surgical data 350 associated with a patient 312, an operating room camera 334, and an operating room microphone 336, and additional operating room tools not illustrated in FIG. 3. Local server 370 receives the data from the computing device 360 over a connection 362 (e.g., wired or wireless) and a surgical data structure from a remote server 380.

In some instances, the computing device 360 can process the data (e.g., to identify and/or characterize a presence and/or position of one or more tools using a trained machine-learning model, to identify a procedural state using a trained machine-learning model or to train a machine-learning model). The computing device 360 can process the metadata corresponding to a procedural state identified as corresponding to live data and generate real-time guidance information for output to the appropriate devices. Also, local server 370 can include one or more components of the machine-learning processing system. Local server 370 can process the metadata corresponding to a procedural state identified as corresponding to live data and generate real-time guidance information for output to the control center 372.

The computing device 360 can be in contact with and synced with a remote server 380. In some embodiments, remote server 380 can be located in the cloud 306. In some embodiments, remote server 380 can process the live data (e.g., to identify and/or characterize a presence and/or position of one or more tools using a trained machine-learning model, to identify a procedural state using a trained machine-learning model or to train a machine-learning model). Remote server 380 can include one or more components of the machine-learning processing system. Remote server 380 can process the metadata corresponding to a procedural state identified as corresponding to live data and generate real-time guidance information for output to the appropriate devices in operating room 302.

A global bank of surgical procedures, described using surgical data structures, may be stored at remote server 380. Therefore, for any given surgical procedure, there is the option of running system 300 as a local, or cloud-based system. The computing device 360 can create a surgical dataset that records data collected during the performance of a surgical procedure. The computing device 360 can analyze the surgical dataset or forward the surgical dataset to remote server 380 upon the completion of the procedure for inclusion in a global surgical dataset. In some embodiments, the computing device 360 can anonymize the surgical dataset in real-time or up the completion of the procedure. System 300 can integrate data from the surgical data structure and sort guidance data appropriately in the operating room using additional components.

In certain embodiments, surgical guidance, retrieved from the surgical data structure, may include more information than necessary to assist the surgeon with situational awareness. The system 300 may determine that the additional operating room information may be more pertinent to other members of the operating room and transmit the information to the appropriate team members. Therefore, in certain embodiments, system 300 provides surgical guidance to more components than a conventional display 330.

In certain embodiments, surgical guidance, retrieved from the surgical data structure, may include more information than necessary to assist the surgeon with situational awareness. The system 300 may determine that the additional operating room information may be more pertinent to other members of the operating room and transmit the information to the appropriate team members. Therefore, in certain embodiments, system 300 provides surgical guidance to more components than a conventional display 330.

In the illustrated embodiment, mobile devices 331, such as smartphones and tablets, and wearable devices, such as a surgeon's headset 310, a first additional headset 320 and a second additional headset 322, are included in the system 300. Other members of the operating room team may benefit from receiving information and surgical guidance derived from the surgical data structure on the mobile and wearable devices. For example, a surgical nurse wearing first additional headset 320 or having a mobile device 331 in the close vicinity may benefit from guidance related to procedural steps and possible equipment needed for impending steps. An anesthetist wearing second additional headset 322 or having a mobile display 331 in the close vicinity may benefit from seeing the patient vital signs in the field of view. In addition, the anesthetist may be the most appropriate user to receive the real-time risk indication as one member of the operating room slightly removed from surgical action.

Various peripheral devices can further be provided, such as conventional displays 330, transparent displays that may be held between the surgeon and patient, ambient lighting 332, one or more operating room cameras 334, one or more operating room microphones 336, speakers 340 and procedural step notification screens placed outside the operating room to alert entrants of critical steps taking place. These peripheral components can function to provide, for example, state-related information. In some instances, one or more peripheral devices can further be configured to collect image data.

The computing device 360 may use one or more communications networks to communicate with operating room devices including (for example) wired connections (e.g., Ethernet connections) or various wireless protocols, such as IrDA™, Bluetooth™, Zigbee™ Ultra-Wideband, and/or Wi-Fi. In some embodiments, existing operating room devices can be integrated with system 300. To illustrate, once a specific procedural location is reached, automatic functions can be set to prepare or change the state of relevant and appropriate medical devices to assist with impending surgical steps. For example, operating room lighting 332 can be integrated into system 300 and adjusted based on impending surgical actions indicated based on a current procedural state.

In some embodiments, system 300 may include a centralized hospital control center 372 and a central hospital local server 370. The control center 372 through the hospital local server 370 may be connected to one, more or all active procedures and coordinate actions in critical situations as a level-headed, but skilled, bystander. Control center 372 may be able to communicate with various other users via user-specific devices (e.g., by causing a visual or audio stimulus to be presented at a headset) or more broadly (e.g., by causing audio data to be output at a speaker in a given room 302.

In some instances, methods and systems are provided for performing anonymization of one or more data streams from the surgical procedure in an real-time process or an offline process. In some embodiments, the computing device 360 or a remote server 380 can anonymize and store the one or more data streams from a surgical procedure. Data streams (e.g., video streams) from a surgical procedure contain sensitive or confidential information such as patient identification, voice data, facial features, and other sensitive personal information about the patient and/or operating room personnel. In some embodiments, the method includes anonymizing and protecting the identity of all medical professionals, patients, distinguishing objects or features in a medical, clinical or emergency unit. The methods and systems can detect facial features, objects, or features in a medical, clinical or emergency unit and distort or blur or colorize (e.g., black) or remove the image of the distinguishing element. In some embodiments, the extent of the distortion/blur/colorization is limited to a localized area, frame by frame, to the point where identity is protected without limiting the quality of the analytics.

Figure 4:
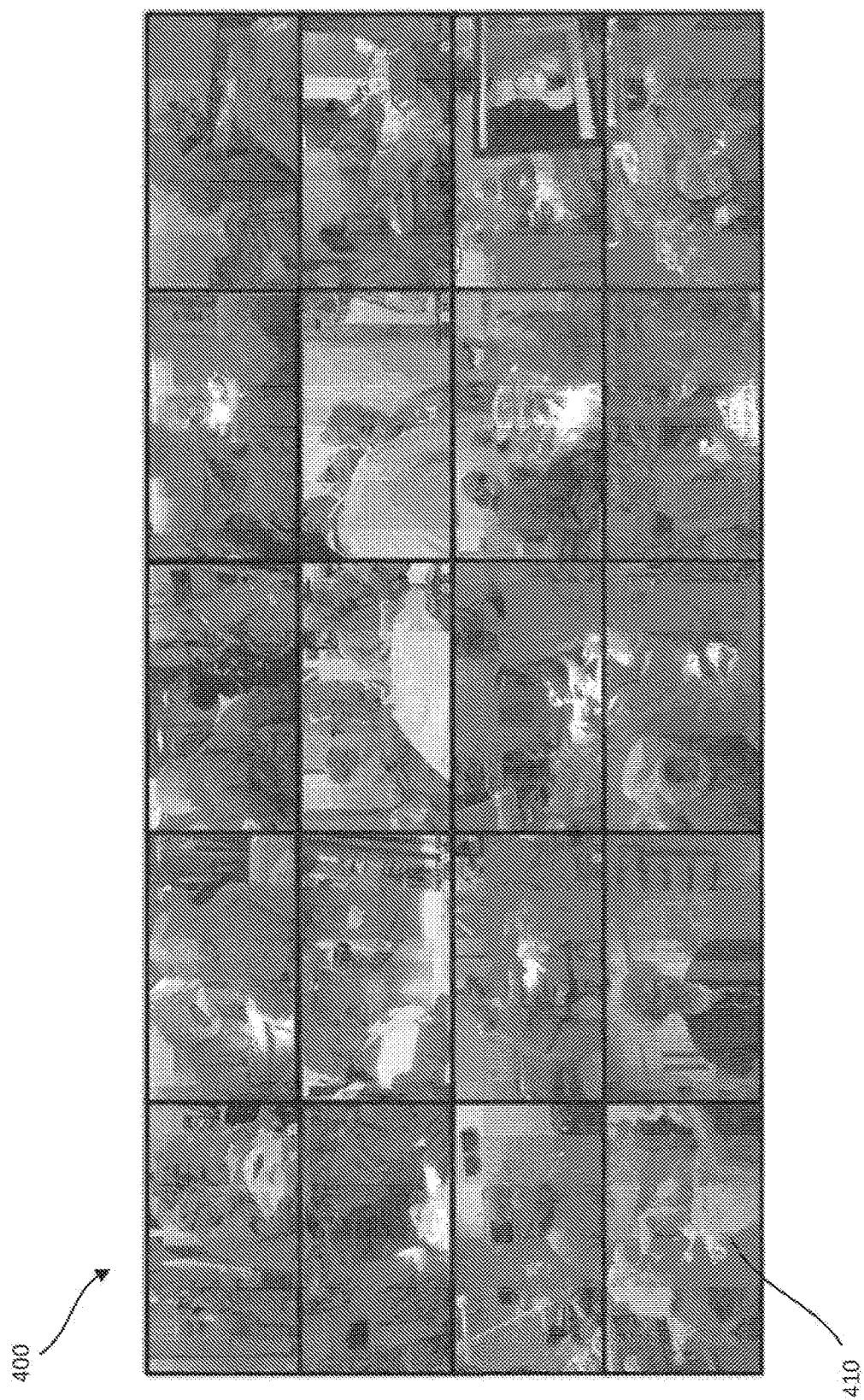
FIG. 4 shows a collection of surgical environments potentially exposing sensitive information from a surgical procedure.

FIG. 4 shows a collection 400 of surgical environments potentially exposing sensitive information from a surgical procedure. The data streams from a surgical procedure can be video data 410. The video data 410 from a surgical procedure can be processed in a machine-learning model to anonymize and/or eliminate information through the identification and removal of (for example) tagged information. In some embodiments, a deep-learning model (e.g., Faster R-CNN) can be used to anonymize data streams from a surgical procedure. For example, the model can detect and blur faces in the data streams to preserve anonymity. The anonymized data streams can be stored and used for a wide range of purposes (for example) documentation, teaching, and surgical data science.

The data streams can be anonymized prior to storage on a server. In some embodiments, Convolutional Neural Networks (CNN) can be used for detection, pose estimation, and emotion prediction. The introduction of large datasets has enhanced robustness and efficiency of deep learning models leading to developments of recurrent CNN (RCNN), Fast-RCNN, and Faster Regions with Convolutional Neural Networks (Faster-RCNN).

In some embodiments, Faster-RCNNs can process the data streams to anonymize (for example) video data captured during a surgical procedure. However, challenges exist with these models for use in a surgical environment because the data needs to be adapted to process a plurality of variables, e.g., masked faces, surgical caps, lighting variability, etc. For example, faces in the operating room are very different than those found in traditional datasets used to train machine-learning models due to masks, caps, and surgical magnifying glasses. Detecting such features require model adaptation. In some embodiments, the methods for anonymization provide a sliding window for temporal smoothing to have a higher chance of detecting any missed information (e.g., a false negative). In some embodiments, a new dataset can be used to train a machine-learning model to account for variables in a surgical environment, and can be fine-tuned to achieve higher detection rates. For example, datasets for facial recognition used for training machine-learning models can be adapted (e.g., labeled surgical environment data) to fine-tune a machine-learning model.

Figure 5:
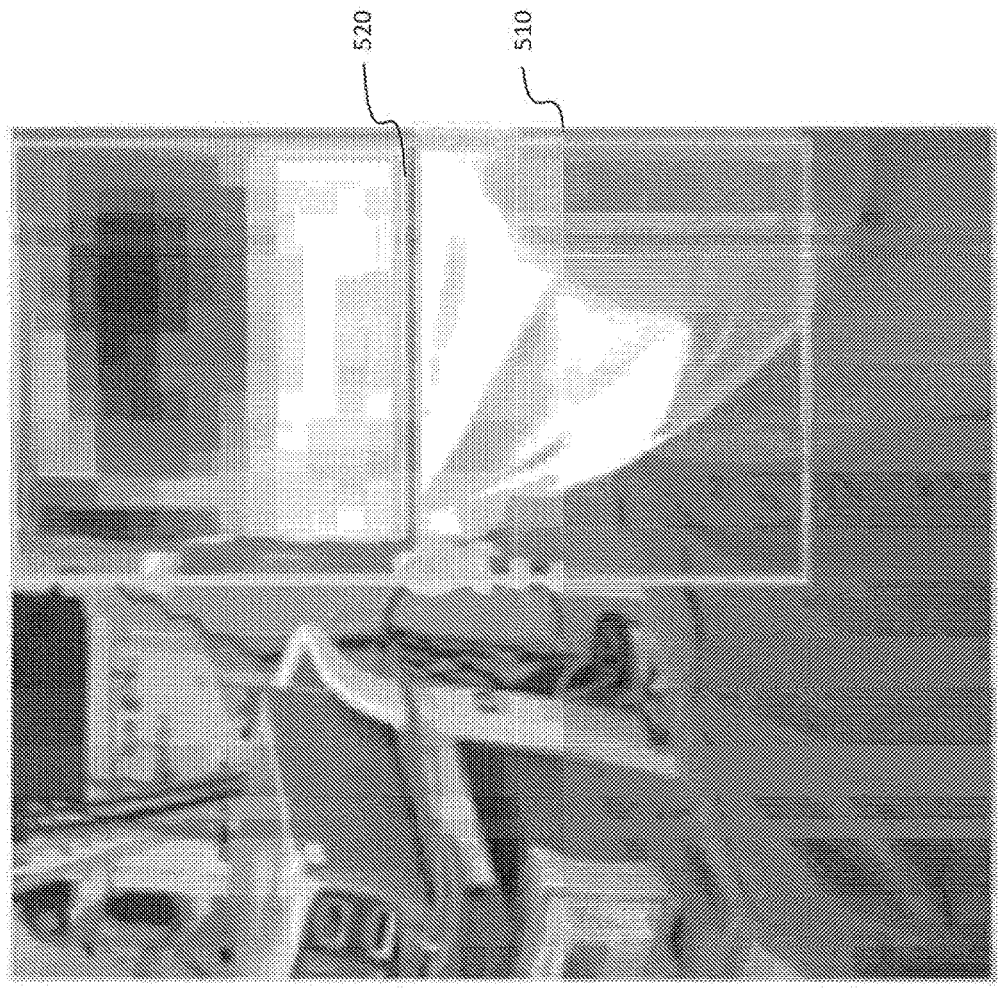
FIG. 5 shows an embodiment for a process of identifying sensitive information and distorting and/or blurring a localized area for anonymization.

FIG. 5 shows one example of identifying sensitive information (e.g., facial features) and augmenting a localized area (e.g., distort, blur, or black-out), frame by frame, to the point where identity is protected without limiting the quality of the analytics. Specifically, FIG. 5 shows an anonymized frame 500 of a video stream. In one example, frame 500 of a video stream is anonymized using Faster-RCNNs. It is also contemplated that the frames of a video stream can be processed using numerous other deep-learning models (e.g., convolutional neural networks, recurrent neural networks, etc.). The aforementioned Faster-RCNN uses a regional proposal network that estimates bounding boxes around an input data stream (e.g., input image). For example, the green bounding box 510 and the pink bounding box 520 describes the ground truth and detected face, respectively. As seen in the image, the anonymization has occurred given the area above the mask was detected represented by the green bounding box 510. The detected region is less than half the area of the annotated face.

In some embodiments, voice and/or voice alteration processes can be used to anonymize and protect the identity of all medical professionals, patients, distinguishing objects or features in a medical, clinical or emergency environment. This software may implement methods and techniques running on hardware in a medical, clinical or emergency environment to alter voices, conversations and/or remove statements of everyday language to preserve the identity of the speaker while at the same time maintaining the integrity of the input stream so as to not adversely impact the quality of the analytics.

Eliminating sensitive data involves the anonymizing of data through the identification and removal of (for example) tagged information. For example, information such as patient identification, voice data, facial features, and other sensitive personal information about the patient and/or operating room personnel can be eliminated from the one or more data streams. To address privacy concerns, the artificial intelligence system can anonymize data in real time and the anonymized data streams are stored. In some instances, the one or more data streams can be processed at a central server to anonymize data in real time. The anonymization can include (for example) discarding speech used in the operating room and only storing sounds that are associated with particular surgical steps.

In some embodiments, live surgical data (or a processed version thereof, such as timestamped state identification) can be preserved for a post-hoc analysis (e.g., off-line analysis). To improve the security corresponding to the live data, the data may be stored so as to anonymize the data and/or to obscure and/or encrypt particular (e.g., private or identifying) features. Live surgical data may be processed to identify current procedural states throughout the surgery.

Figure 6:
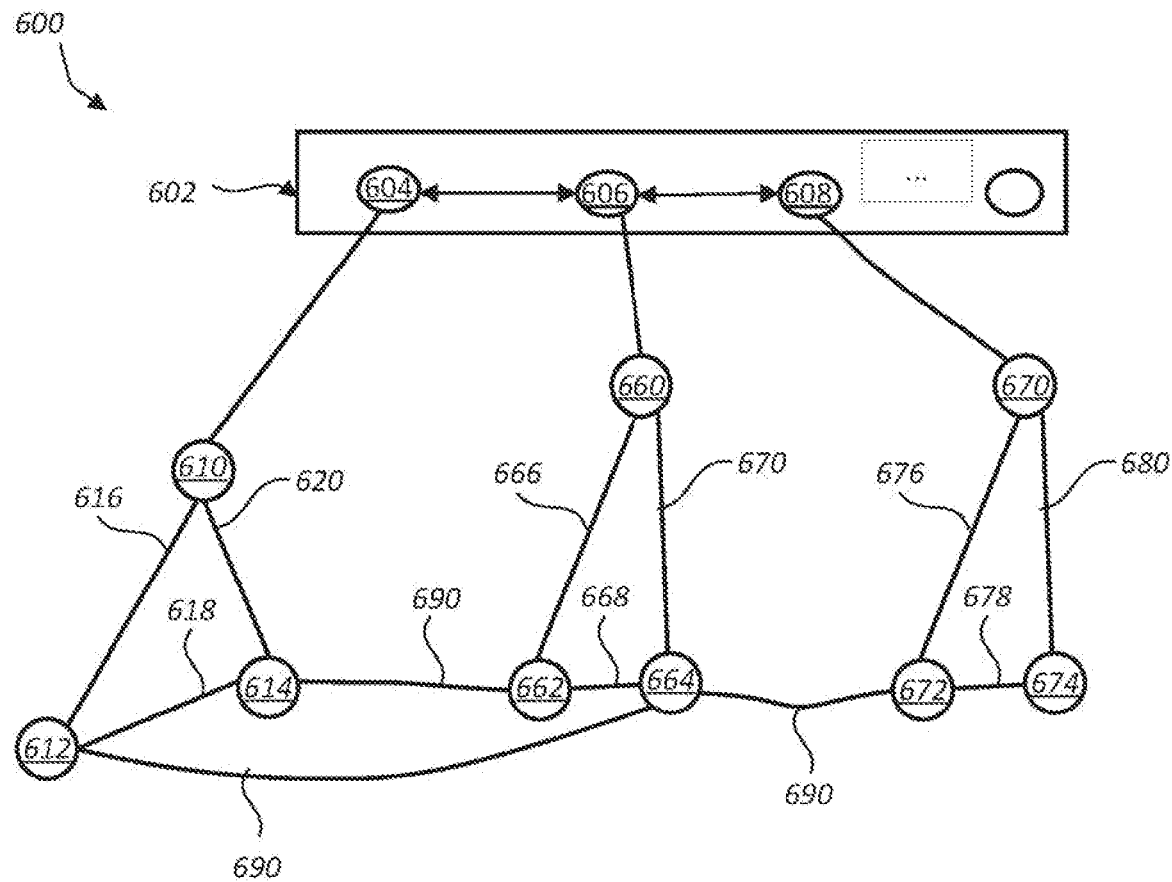
FIG. 6 shows an embodiment of a global surgical map for multiple interconnected surgical data structures.

FIG. 6 illustrates an embodiment of a surgical map 600 including multiple data structures 604, 606, 608. In some embodiments, the multiple data structures 604, 606, 608 described herein include a global surgical graph 602 that may include a map (e.g., nodes and edges) to a plurality of interconnected surgical data structures 604, 606, 608. Each of the surgical data structures 604, 606, 608 may represent a set of characteristics for a surgical procedure (e.g., cataract surgery, heart bypass, sleeve gastrectomy, hip replacement, etc.). Each of the surgical data structures 604, 606, 608 are interconnected (e.g., nodes are connected by edges) such that additional information for portions (e.g., segments of a video stream) of the surgical procedure can be identified. For example, the first data structure 604 can identify a set of procedural stages in the surgical procedure represented by nodes 610, 612, 614 and the second data structure 606 can identify a set of surgical tools in the surgical procedure represented by nodes 660, 662, 664. The first data structure 604 may include one or more nodes 612, 614 that are connected by edges 690 to one or more nodes 662, 664 of the second data structure 606. The edges 690 connecting the first data structure 604 to the second data structure 606 can provide additional relational metadata about the surgical procedure via the edges 690 connecting the nodes of each data structure 604, 606 (for example) including a risk, tools being used or that are about to be used, and/or a warning. Similarly, the second data structure 606 may include node 664 that is connected by edge 690 to one or more node 672 of the third data structure 608. It is also contemplated that any of the nodes 610, 612, 614 for the first data structure 604 can be connected by edge 690 to any of the nodes 670, 672, 674 of the third data structure 608. Each of the surgical data structures 604, 606, 608 can be connected in multiple ways as long as there are interconnections (e.g., edges) between the surgical data structures 604, 606, 608.

The surgical map 600 may process surgical data using metadata (e.g., procedural state, surgical tools, anatomical features, surgical actions, etc.) associated with nodes or edges from each of the surgical data structures 604, 606, 608. Additionally, the surgical map 600 may transition from a first data structure 604 to another surgical data structure (e.g., the second data structure 606 or the third data structure 608) in the global surgical graph 602. For example, during a surgical procedure, the global surgical graph 602 can include a first surgical data structure 604, a second surgical data structure 606, and a third surgical data structure 608, each associated with a set of characteristics of a surgical procedure. The first surgical data structure 604 begins at node 610, which includes (for example) a description of and/or information corresponding to a procedural state. The second surgical data structure 606 begins at node 660, which includes (for example) a description of and/or information corresponding to surgical tools (e.g., scalpel, forceps, stapler, etc.) associated with a procedural state. The third surgical data structure 608 begins at node 670, which includes (for example) a description of and/or information corresponding anatomical features (e.g., heart, spleen, kidney, etc.) associated with a procedural state. Each of these surgical data structures 604, 606, 608 may include nodes that are connected by edges. The edges indicate a transition from one node to the next node (e.g., from a first procedural state to a second procedural state). The first, second, and third surgical data structure 604, 606, 608 may include multiple interconnected nodes that provide inter-relational information between each of the surgical data structures. In some embodiments, the systems and methods described herein may automatically transition between the surgical data structures 604, 606, 608 included in the global surgical graph 602.

In some embodiments, the first surgical data structure 604 may start at node 610 and represent procedural states of a surgical procedure. The first surgical data structure 604 may include a plurality of nodes 610, 612, 614 representing each procedural stage of the surgical procedure. The edges 616, 618, 620 between each of nodes may represent metadata (for example) including medical personnel and/or tools necessary to perform the procedural action. A first procedural state may be associated with a first node 610, a second procedural state is associated with a second node 612, and a third procedural state may be associated with a third node 614. The first edge 616 is associated with a set of procedural metadata and includes a description of and/or information corresponding to the first procedural state. For example, the first edge 616 includes metadata associated with a change from a first procedural state (e.g., node 610) to a second procedural state (e.g., node 612).

The second surgical data structure 606 may start at node 660 and may represent (for example) one or more surgical tools used in the surgical procedure. Second surgical data structure 604 may include a plurality of nodes 660, 662, 664 where each node represents a specific surgical tool of the surgical procedure. In some cases, surgical tools are associated with nodes 660, 662, 664 and actions (e.g., movement, appearance, spatial location, etc.) with respect to the surgical tools are associated with the edges 666, 668, 670. For example, each of the edges 666, 668, 670 can represent when a surgical tool is stationary, when a surgical tool is in contact with an anatomical feature, when a surgical tool is being used by a surgeon, etc. The nodes 660, 662, 664 are connected by edges 666, 668, 670 which represent surgical interactions related to the associated node-to-node transition.

The third surgical data structure 608 may start at node 670 and represent one or more anatomical features (e.g., heart, spleen, kidney, etc.) in the surgical procedure. Third surgical data structure 608 may include a plurality of nodes 670, 672, 674 representing anatomical features during the surgical procedure. In some aspects, each of the nodes 670, 672, 674 may represent one or more different anatomical features and may include a sub-tree of nodes associated with each different anatomical feature. In some cases, anatomical features are associated with nodes 670, 672, 674 and characteristics (e.g., incisions, movement, shape, etc.) of the anatomical features are associated with edges 676, 678, 680. For example, each of the edges 676, 678, 680 can represent when an anatomical structure is incised, moved, removed, etc. The nodes 670, 672, 674 are connected by edges 676, 678, 680 which can represent surgical interactions with the anatomical features related to the associated node-to-node transition.

Edges 690 represent nodes from each surgical data structure 604, 606, 608 that are interconnected. For example, nodes 612, 614 from the first data structure 604 can be connected (e.g., via edges 690) to the nodes 662, 664 of the second data structure 606 and, optionally, nodes 672, 674 of the third data structure 608 (not shown). Edges 690 interconnecting the nodes of each surgical data structure 604, 606, 608 may include information included in or identified by metadata. Edges 690 between nodes for each surgical data structure 604, 606, 608 may (for example) identify the procedural state (e.g., by identifying a state of a patient, progress of a surgery, etc.), identify an action that is being performed or is about to be performed (e.g., as identified in an edge that connects a node corresponding to the procedural state with a node corresponding to a next procedural state), and/or identify one or more considerations (e.g., a risk, tools being used or that are about to be used, a warning, etc.).

In some embodiments, the surgical data structures can identify a surgical action based on weights assigned to one or more edges between the node-to-node transitions. In some embodiments, a weight may be assigned to each node in addition to, or in lieu of, the weight assigned to each edge. The weights may be associated with a plurality of factors including, (for example) surgical outcomes, risk, prevalence of use, current procedural state, patient characteristics, vital signs, procedure specific parameters, and/or user (e.g., surgeon, nurse or team member) experience. The risk may be based on maximum risk or a risk based on the probability of occurrence. The weights may be manually assigned when constructing the surgical data structure. In other embodiments, the surgical weights may be determined or updated using a machine learning algorithm based on collected surgical data, including surgical outcomes.

To further illustrate the use of multiple interconnected surgical data structures, an embodiment describing a subset of steps performed during the surgical procedure for sleeve gastrectomy is provided herein. Sleeve gastrectomy is a procedure for removing a portion of the stomach to promote weight loss. In this procedure, portions of the stomach are removed to take on the shape of a tube or "sleeve" which holds less food.

Figure 7:
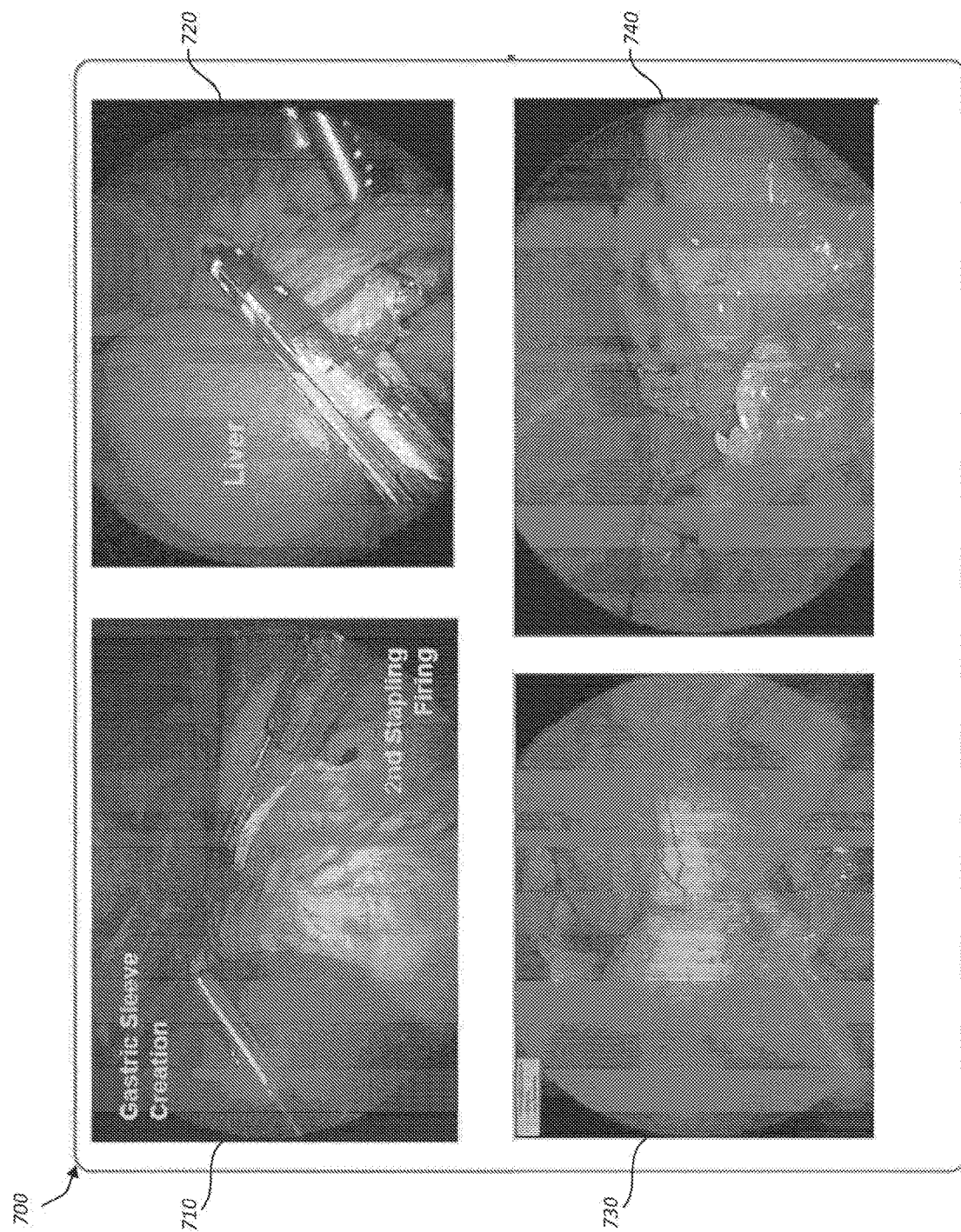
FIG. 7 shows an embodiment for processing surgical data using multiple interconnected surgical data structures.

FIG. 7 shows a process for using multiple data structures to process surgical data to produce and/or update an electronic output. In one embodiment, portions of a video stream 700 from a surgical procedure can be processed using multiple interconnected data structures. In some embodiments, the multiple interconnected data structures can include multiple different data structures representing different characteristics of a surgical procedure. For example, the data structures may correspond to at least one of anatomical features in a surgical procedure, procedural stages of a surgical procedure, and/or surgical tools in a surgical procedure. Each of these distinct data structures may include interconnected nodes that provide relational metadata that is not available in a single data structure. For example, a data structure corresponding to the procedural stages of a surgical procedure may only provide information regarding the detection of a surgical instrument, but does not provide spatial and/or temporal information regarding the medical personnel or surgical instrument. The metadata between interconnected nodes of different data structures may provide relational metadata to provide this additional information.

In some embodiments, the surgical data can include video streams from a sleeve gastrectomy procedure. FIG. 7 shows portions of a video stream 700 of a sleeve gastrectomy procedure processed using the multiple interconnected data structures. For example, a first data stream 710, a second data stream 720, a third data stream 730, and a fourth data stream 740 from a sleeve gastrectomy procedure can each be processed using the multiple interconnected data structures. The first data stream 710 can be processed to identify a stage of sleeve gastrectomy, e.g., surgical workflow detection, according to a first data structure. The first surgical data structure can provide precise and accurate descriptions of complete surgical procedures for sleeve gastrectomy. The first surgical data structure can describe routes through surgical procedures. For example, the first surgical data structure can include multiple nodes, each node representing a procedural state (e.g., corresponding to a state of a patient). The surgical data structure can further include multiple edges, with each edge connecting multiple nodes and representing a surgical action.

Similarly, the second data stream 720, the third data stream 730, and the fourth data stream 740 can be processed using other data structures of the multiple interconnected data structures. For example, the second data stream 720 can be processed to identify anatomical features detected during the sleeve gastrectomy procedure using a second data structure. The second data structure can provide precise and accurate descriptions of anatomical features in a sleeve gastrectomy procedure. The third data stream 730 can be processed to identify surgical instruments detected during the sleeve gastrectomy procedure using a third data structure and the fourth data stream 740 can be processed to identify surgical events during the sleeve gastrectomy procedure. Each portion of the video stream 700 can be processed using a multi-dimensional artificial intelligence protocol as described herein.

Each of the data structures may include a plurality of nodes connected to nodes in another data structure representing additional characteristics of a sleeve gastrectomy procedure. For example, a second data structure may represent the anatomical features present in the sleeve gastrectomy procedure and a third data structure may represent the surgical tools used in the sleeve gastrectomy procedure. The interconnected nodes in each of these data structures can provide relational metadata regarding the surgical procedure sleeve gastrectomy procedure. For example, in fourth data stream 740, the relational metadata between the multiple data structures can provide relevant information that is aggregated over time. The relational metadata can provide information (for example) including usage of surgical tools near anatomical features that may cause injury, prolonged usage of surgical instruments, medical personnel at specific stages of surgery, or actions/events at specific stages of surgery. This information can be compiled and output as an electronic output (e.g., an operational note).

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

What is claimed is:

1. A computer-implemented method comprising:
   accessing, by a processor, a surgical dataset associated with a surgical procedure, the surgical dataset comprising a surgical video of the surgical procedure being performed using a surgical tool;
   creating, by the processor, a surgical map of the surgical procedure by analyzing the surgical video using a trained machine learning algorithm that is trained using training data with pixel-level labels from a segmented procedure video stream, wherein the surgical map comprises at least:
      a first data structure that comprises a first plurality of nodes and a first plurality of edges, wherein a first node from the first data structure represents a procedural state in the surgical procedure;
      a second data structure that comprises a second plurality of nodes and a second plurality of edges, wherein a second node from the second data structure represents the surgical tool used in the surgical procedure;
   adding, by the processor, an interconnecting edge between the first node and the second node based on a surgical event detected in the surgical video, wherein the interconnecting edge is associated with a relational metadata representing a use of the surgical tool of the second node in the procedural state of the first node;
   augmenting, by the processor, the surgical video by including an electronic data to a portion of the surgical video comprising a set of pixels, the electronic data describing an operational note based at least on the procedural state of the first node, a data associated with the second node, and the relational metadata associated with the interconnecting edge between the first node and the second node, the portion comprising the use of the surgical tool of the second node in the procedural state of the first node; and
   outputting, by the processor, the electronic data during playback of the portion of the surgical video on a display.

2. The computer-implemented method of claim 1, wherein the surgical dataset further comprises one or more data streams captured during the surgical procedure, each of the one or more data streams obtained from a corresponding data capture device, wherein the one or more data streams comprise:
   video streams captured by one or more cameras;
   audio streams captured by one or more microphones; and/or
   signals from electronic devices comprising medical equipment used during the surgical procedure.

3. The computer-implemented method of claim 2, wherein the electronic data is associated with a second portion of at least one of the one or more data streams, the second portion corresponding to the use of the surgical tool of the second node in the procedural state of the first node.

4. The computer-implemented method of claim 2, wherein the one or more data streams further comprise user inputs provided by operating room personnel via a wearable device or non-wearable device located inside or near an operating room while the surgical procedure is performed.

5. The computer-implemented method of claim 1, wherein the first plurality of edges in the first data structure represents a transition of procedural states during the surgical procedure.

6. The computer-implemented method of claim 1, wherein the surgical map comprises additional data structures, each additional data structure comprising a plurality of nodes and a plurality of edges.

7. The computer-implemented method of claim 1, further comprising updating an electronic medical record to include the electronic data.

8. The computer-implemented method of claim 1, wherein outputting the electronic data during playback of the portion comprises augmenting the surgical video with the electronic data, and either storing an augmented video stream or transmitting the augmented video stream for playback.

9. The computer-implemented method of claim 1, wherein the trained machine learning algorithm uses separate machine learning models for each data structure from the surgical map.

10. A system comprising:
    a multi-dimensional artificial intelligence system;
    a surgical operating system configured to interface with one or more cameras;
    and one or more processors coupled with the multi-dimensional artificial intelligence system, and the surgical operating system, the one or more processors are configured to perform a method comprising:
       accessing a surgical dataset associated with a surgical procedure, the surgical dataset comprising a surgical video of the surgical procedure being performed as captured by the one or more cameras;
       creating a surgical map of the surgical procedure by analyzing the surgical video using the multi-dimensional artificial intelligence system that is trained using training data with pixel-level labels from a segmented procedure video stream, wherein the surgical map comprises at least:
          a first data structure that comprises a first plurality of nodes and a first plurality of edges, wherein a first node from the first data structure represents a first procedural feature of the surgical procedure; and
          a second data structure that comprises a second plurality of nodes and a second plurality of edges, wherein a second node from the second data structure represents second procedural feature of the surgical procedure;

adding an interconnecting edge between the first node and the second node based on a surgical event detected in the surgical video, wherein the interconnecting edge is associated with a relational metadata representing a use of the first procedural feature of the first node in connection with the second procedural feature of the second node;

augmenting the surgical video by including an electronic data to a portion of the surgical video comprising a set of pixels, wherein the electronic data describes an operational note based at least on the first procedural feature, the second procedural feature, and the relational metadata associated with the interconnecting edge between the first node and the second node, the portion comprising the use of the first procedural feature in connection with the second procedural feature; and outputting the electronic data during playback of the portion of the surgical video on a display.

11. The system of claim 10, wherein the first data structure and the second data structure represent one from a group of procedural features comprising procedural states, surgical tools, anatomical structures, phonemes, medical personnel, and surgical actions.

12. The system of claim 10, wherein outputting the electronic data during playback of the portion comprises augmenting the surgical video with the electronic data, and either storing an augmented video stream or transmitting the augmented video stream for playback.

13. The system of claim 10, wherein the surgical dataset further comprises one or more data streams captured during the surgical procedure, each of the one or more data streams obtained from a corresponding data capture device.

14. The system of claim 13, wherein the electronic data is associated with a second portion of at least one of the one or more data streams, the second portion corresponding to the use of the second procedural feature of the second node with the first procedural feature of the first node.

15. The system of claim 13, wherein the one or more processors are further configured to update an electronic medical record to include the operational note.

16. A computer program product comprising a non-transitory computer storage medium having computer executable instructions stored thereon, the computer executable instructions when executed by one or more processors cause the one or more processors to perform a method comprising:

creating a surgical map of a surgical procedure by analyzing a surgical video of the surgical procedure using a trained machine learning algorithm that is trained using training data with pixel-level labels from a segmented procedure video stream, wherein the surgical map comprises at least:

a first data structure that comprises a first plurality of nodes, wherein a first node from the first data structure represents a first procedural feature of the surgical procedure; and a second data structure that comprises a second plurality of nodes, wherein a second node from the second data structure represents second procedural feature of the surgical procedure;

adding an interconnecting edge between the first node and the second node based on a surgical event detected in the surgical video, wherein the interconnecting edge is associated with a relational metadata representing a use of the first procedural feature of the first node in connection with the second procedural feature of the second node;

augmenting the surgical video by including an electronic data to a portion of the surgical video comprising a set of pixels, the electronic data describing an operational note based at least on the first procedural feature, the second procedural feature, and the relational metadata associated with the interconnecting edge between the first node and the second node, the portion of the surgical video comprising the use of the first procedural feature in connection with the second procedural feature; and outputting the electronic data during playback of the portion of the surgical video on a display.

17. The computer program product of claim 16, wherein the surgical video is streamed live.

18. The computer program product of claim 16, wherein the surgical video is accessed from a storage device.

19. The computer program product of claim 16, wherein the method further comprises updating an electronic medical record to include the operational note.

* * * * *